US007217863B2

(12) United States Patent
Famodu et al.

(10) Patent No.: US 7,217,863 B2
(45) Date of Patent: May 15, 2007

(54) MEVALONATE SYNTHESIS ENZYMES

(75) Inventors: Omolayo O. Famodu, Newark, DE (US); William D. Hitz, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 61 days.

(21) Appl. No.: 11/062,007

(22) Filed: Feb. 18, 2005

(65) Prior Publication Data

US 2005/0183164 A1    Aug. 18, 2005

Related U.S. Application Data

(60) Division of application No. 10/142,835, filed on May 10, 2002, now Pat. No. 6,916,972, which is a continuation-in-part of application No. 09/433,982, filed on Nov. 4, 1999, now abandoned.

(60) Provisional application No. 60/107,277, filed on Nov. 5, 1998.

(51) Int. Cl.
*A01H 1/00* (2006.01)
*C07H 21/04* (2006.01)
*C07K 14/415* (2006.01)
*C12N 5/14* (2006.01)
*C12N 9/00* (2006.01)

(52) U.S. Cl. .................. 800/295; 435/6; 435/69.1; 435/468; 435/419; 435/252.3; 435/320.1; 435/183; 530/370; 536/23.6; 800/278

(58) Field of Classification Search ................ 435/6, 435/69.1, 468, 419, 252.3, 320.1, 183; 530/370; 536/23.6; 800/278, 296
See application file for complete search history.

(56) References Cited

OTHER PUBLICATIONS

Douglas J. McGarvey et al., The Plant Cell, vol. 7:1015-1028, Jul. 1995, Terpenold Metabolism.
Akira Honda et al., Journal of Lipid Research, vol. 39:44-50, 1998, Down-regulation of cholesterol biosynthesis in sitosterolemia: diminished activities of acetoacetyl-CoA thiolase, 3-hydroxy-3-methylglutaryl-CoA synthase, reductase, squalene synthase, and 7-dehydrocholesterol $\Delta^7$-reductase in liver and mononuclear leukocytes.
Rodney Croteau et al., Archives of Biochemistry and Biophysics, vol. 271:524-535, Jun. 1989, Geranyl Pyrophate Synthase: Characterization of the Enzyme and Evidence That This Chain-Length Specific Prenyltransferase Is Associated with Monoterpene Biosynthesis in Sage.
Thomas J. Bach, Lipids, vol. 21:82-88, 1986, Hydroxymethylglutaryl-CoA Reductase, a Key Enzyme in Phytosterol Synthesis?.
Thomas J. Bach, Plant Physiol. Biochem. vol. 25:163-178, 1987, Synthesis and metabolism of mevalonic acid in plants.
Montserrat Enjuto et al., Proc. Natl. Acad. Sci. USA, vol. 91:927-931, 1994, Arabidopsis thaliana contains two differentially expressed 3-hydroxy-3-methylglutaryl-CoA reductase genes, which encode microsomal forms on the enzyme.
Lenka Biardi et al., The Journal of Biochemical Chemistry, vol. 271:1784-1788, 1996, Compartmentalization of Cholesterol Biosynthesis.
National Center for Biotechnology Information General Identifier No. 5531937, Jul. 20, 1999, Moon, J. S. et al., Identification of maize acetoacetyl CoA thiolase from developing maize embryo.
National Center for Biotechnology Information General Identifier No. 5607829, Jul. 27, 1999, Walbot, V., Maize ESTs from various cDNA libraries sequenced at Stanford University.
National Center for Biotechnology Information General Identifier No. 6021192, Mar. 30, 2000, Walbot, V., Maize ESTs from various cDNA libraries sequenced at Stanford University.
National Center for Biotechnology Information General Identifier No. 5607308, Jul. 27, 1999, Yamamoto, K. et al., Rice cDNA from callus. (1998).
National Center for Biotechnology Information General Identifier No. 3763023, Oct. 19, 1998, Sasaki, T. et al., Rice cDNA from panicle.
National Center for Biotechnology Information General Identifier No. 426049, Jul. 8, 1999, Sasaki, T. et al., Rice cDNA from callus.
National Center for Biotechnology Information General Identifier No. 3107208, May 4, 1998, Uchimiya, H., On nucleotide sequence of Oryza sativa.
National Center for Biotechnology Information General Identifier No. 2443029, Sep. 29, 1997, Sasaki, T. et al., Rice cDNA from Immature leaf including apical meristem.
National Center for Biotechnology Information General Identifier No. 5761388, Dec. 13, 1999, Shoemaker, R. et al., Public Soybean EST Project.
Andreas P. Russ et al., Biochimica et Biophysical Acta. vol. 1132:329-331, 1992, Amplification and direct sequencing of a cDNA encoding human cytosolic 3-hydroxy-3-methylglutaryl-coenzyme A synthase.
National Center for Biotechnology Information General Identifier No. 5030550, Feb. 2, 2000, Walbot, V., Maize ESTs from various cDNA libraries sequenced at Stanford University.
National Center for Biotechnology Information General Idenifier No. 6012290, Oct. 5, 1999, Walbot, V., Maize ESTs from various cDNA libraries sequenced at Stanford University.
National Center for Biotechnology Information General Identifier No. 5901402, Sep. 15, 1999, Walbot, V., Maize ESTs from various cDNA libraries sequenced at Stanford University.
National Center for Biotechnology Information General Identifier No. 3760977, Oct. 19, 1998, Sasaki, T. et al., Rice cDNA from Callus.
National Center for Biotechnology Information General Identifier No. 2427448, Sep. 22, 1997, Sasaki, T. et al., Rice cDNA from panicle at flowering stage.

(Continued)

*Primary Examiner*—Phuong T. Bui

(57) ABSTRACT

This invention relates to an isolated nucleic acid fragment encoding a mevalonate synthesis enzyme. The invention also relates to the construction of a chimeric gene encoding all or a portion of the mevalonate synthesis enzyme, in sense or antisense orientation, wherein expression of the chimeric gene results in production of altered levels of the mevalonate synthesis enzyme in a transformed host cell.

13 Claims, 6 Drawing Sheets

OTHER PUBLICATIONS

National Center for Biotechnology Information General Identifier No. 428081, Jul. 8, 1999, Minobe, Y. et al., Rice cDNA from root.

National Center for Biotechnology Information General Identifier No. 454498, Jul. 8, 1999, Sasaki, T. et al., Rice cDNA from callus.

National Center for Biotechnology Information General Identifier No. 1542941, Sep. 13, 1996, Vollack, K. U. et al., Cloning of a cDNA encoding cytosolic acetoacetyl-coenzyme A thiolase from radish by functional expression in *Saccharomyces cerevislae*.

National Center for Biotechnology Information General Identifier No. 5531937, Jul. 20, 1999, Moon, J. S. et al., Identification of maize acetoacetyl Coa thiolase from developing maize embryo.

National Center for Biotechnology Information General Identifier No. 1708236, Oct. 1, 1996, Montamat, F. et al., Isolation and characterization of a cDNA encoding *Arabidopsis thaliana* 3-hydroxy-3-methylglutary-coenzyme A synthase.

Vollack et al. Plant Physiol. vol. 111, vet. No. 4:1097-1107, (1996).

Florence Montamat et al., Gene, vol. 167:197-201, 1995, Isolation and characterization of a cDNA encoding *Arabidopsis thailana* 3-hydroxy-3-methylglutaryl-coenzyme A synthase.

Hiroshi Watanabe et al., Tohoku J. Exp. Med., vol. 184:29-38, 1998, Practical Assay Method of Cytosolic Acetoacetyl-CoA Thiolsae by Rapid Release of Cytosolic Enzymes from Cultured Lymphocytes using Digitonin.

Hubert Scharnagl et al., Journal of Lipid Research, vol. 36:622-627, 1995, A novel assay for cytosolic 3-hydroxy-3-methylglutaryl-coenzyme A synthase activity using revered-phase ion-pair chromatography: demonstration that Lifibrol (K12.148) modulated the enzyme activity.

Russel et al., Journal of Molecular Biology, vol. 244:332-350, 1994.

National Center for Biotechnology Information General Identifier No. 16417956. Oct. 25, 2001, Hallahan, D.L. and Kelper-Hrynko, N.M. Genes involved in the biosynthesis of isopentenyl diphosphate in the rubber tree *Hevea brasiliensis*.

FIG. 1A

```
                      **   ****  ******************   ****** *****   * *** *
SEQ ID NO:33          MAHSADSSDN---PRDVCIVGVARTPMGGFLGSLSSLPATKLGSLAITAALKREMLTRLW
SE3 ID NO:34          ------------------------------------------------------------
SE3 ID NO:18          MAS-------DGIGPRDVCVVGVARTPMGGFLGALSPLPATKLGSIVIQAALERANVDPAL
SE3 ID NO:20          MAS-------DNIGSRDVCVVGVARTPMGGFLGALSSLSATKLGSIAIEAALKRANVDPAL
SE3 ID NO:22          MAPVAAASSDSIKPRDVCIVGVARTPMGGFLGTLSSLSATKLGSIAIEAALKRANVDPSL
SE3 ID NO:24          ------------------------------------------------------------
                      1                                                          60

*  *****************   *  *  ****************** * ** ******
SEQ ID NO:33          SKEVVFGNVLSANLGQAPARQAALGAGISNSVICTTVNKVCASGMKAVMIAAQSIQLGIN
SE3 ID NO:34          ------------------------------------------------------------
SE3 ID NO:18          VQEVYFGNVLSANLGQAPARQAALGAGIPNSVVCTTVNKVCASGMKATMFAAQSIQLGIN
SE3 ID NO:20          VQEVFFGNVLSANLGQAPARQAALGAGIPNTVVCSAVNKVCASGMKATMFAAQSILLGIN
SE3 ID NO:22          VEEVFFGNVLSANLGQAPARQAALGAGISNSVICTTVNKVCASGMKAAMLAAQSIQLGTN
SE3 ID NO:24          ------------------------------------------------------------
                      61                                                        120

* *********** ***  ***  ************************* ** ******
SEQ ID NO:33          DVVVAGGMESMSNTPKYLAEARKGSRFGHDSLVDGMLKDGLWDVYNDCGMGSCAELCAEK
SE3 ID NO:34          ------------------------------------------------------------
SE3 ID NO:18          DIVVAGGMESMSNAPKYIAEARKGSRFGHDTLVDAMLKDGLWDVYNDCAMGMCAELCADN
SE3 ID NO:20          DIVVAGGMESMSNAPKYIAEARKGSRFGHDTLVDGMLKDGLWDVYGDFAMGNCAELCADN
SE3 ID NO:22          DVVVAGGMESMSNVPKYLAEARKGSRLGHDSLVDGMLKDGLWDVYKDVGMGVCAELCADN
SE3 ID NO:24          ------------------------------------------------------------
                      121                                                       180
```

FIG. 1B

```
                                *  **  *  * ******   ****  *** *  *** **   **  **
SEQ ID NO:33    FEITREQQDDYAVQSFERGIAAQESGAFTWEIVPVEVSGGRGRPSTIVDKDEGLGKFDAA
SE3 ID NO:34    ---IRHE-----------------------------FAWEIVPIEVPVGRGKPPVLIEKDESLDNFDPA
SE3 ID NO:18    HALTREDQDAFAIQSNERGIAARDSGAFAWEIIPVQVPVGRGKPPTLIERDESLDKFDPV
SE3 ID NO:20    HALTREDQDAYAIQSNERGIAARNSGAFAWEIVPIEVPVGRGKPPVLVDKDEGLDKFDPV
SE3 ID NO:22    HALTRDDQDNYAIQSFERGIAAQESGAFSWEIAPVEVSGGRGRPSTVVDKDEGLGKFDAA
SE3 ID NO:24    ---------------------------FAWEIVPIEVPVGRGKPAVLVDKDESLDKFDAA
                                                                                240
                181

** *****  ***     *    *                  * **  *    **  **  **** *
SEQ ID NO:33    KLRKLRPSFKENGGTVTAGNASSISDGAAAIVLVSGEKALQLGLQVLAKVKGYGDAAQEP
SE3 ID NO:34    KLKKLRPSFKENGGTVTAGNASSISDGAAAALVLVSGQKAQELGLQVLARIRGYADAAQAP
SE3 ID NO:18    KLKKLRPSFKENGGTVTAGNASSISDGAAAALVLVSGQKAQELGLQVLARIKGYADAAQAP
SE3 ID NO:20    KLKKLRPSFKENGGTVTAGNASSISDGAAAALVLVSGQKAQELGLQVIARIKGFADAAQAP
SE3 ID NO:22    KLRKLRPSFKETGGSVTAGNASSISDGAAAALVLVSGEKALKLGLQVIAKITGYADAAQEP
SE3 ID NO:24    KLKKLRPAFKENAGTVTAGNASSISDGAAAALVLVSGKKAQELGLQVLARIKGFADAAQAP
                                                                                300
                241

* *** * *******                          *   *******   ** *******
SEQ ID NO:33    EFFTTAPALAIPKAIAPNSPYSESYQVDYYEINEAFAVVALANQKLLGISPEKVNVNGGA
SE3 ID NO:34    ELFTTPALAIPKAISNAGL--ESSHVDFFEINEAFSAVALANQKLLGIPSEKINVHGGA
SE3 ID NO:18    ELFTTPALAIPKAIANAGL--ESSRVDFYEINEAFSAVALANQKLLGIPSEKINVHGGA
SE3 ID NO:20    ELFTTPALAIPKALANAGL--ESSRVDYYEINEAFSAVALANQKLLGIPSEKINVHGGA
SE3 ID NO:22    ELFTTAPSLAIPKAIAKAGL--ETSQIDFYEINEAFAVVALANQKLLGLNSEKVNVHGGA
SE3 ID NO:24    ELFTTPALAIPKALTNAGL--ESSRIDFYEINEAFSAVALANQKLLGIPSEKINVHGGA
                                                                                360
                301
```

FIG. 1C

```
              *  ******************** ****  *    * ** * ******** **
SEQ ID NO:33  VSLGHPLGCSGARILITLLGILKKRNGKYGVGGVCNGGGGASALV------LEVV
SE3 ID NO:34  VSLGHPLGCSGARILVTLLGVLREKGGKIGVAGVCNGGGASVLVSNSHKKHWLEALDM-
SE3 ID NO:18  VSLGHPLGCSGARILVTLLGVTLIGVLRAKSGKIGVAGVCNGGGGASALV------LELA
SE3 ID NO:20  VSLGHPLGCSGARILVTLLGVTLIGVLREKGGKIGVAGVCNGGGGASALV------LELA
SE3 ID NO:22  VALGHPLGCSGARILVTLLGVTLLGVLKQKNGKYGVGGICNGGGGASALV------VELQ
SE3 ID NO:24  VSLGHPLGCSGARILVTLLGVLREKSGKIGVAGVCNGGGGASALV------------
              361                                                       420
```

FIG. 2A

```
                    *    * *****  *  ****** * *  **  *** *** * *******
SEQ ID NO:35        MA--KNVGILAMDIYFPPTCVQQEALEAHDGASKGKYTIGLGQDCLAFCTELEDVISMSF
SEQ ID NO:26        MD-RKDVGILAMDIYFPPSCVQQEALEAHDGASKGKYTIGLGQDCMAFCSEVEDVISMSL
SEQ ID NO:28        MDGRKDVGILAMDIYFPPTCVLQESLEAHDGASKGKYTIGLGQDCMAFCSEVEDVISMSM
SEQ ID NO:30        MA--KNVGILAIDIYFPPTCIQQELLEAHDGASKGKYTIGLGQDCMAFCTEVEDVISMSL
SEQ ID NO:32        ----KDVGILAMDMYFPPTCVQQEALEVHDGASKGKYTIGLGQDCMAFCSEVEDVISMSL
                    1                                                          60

*  ***  **  *   ***************************  **  **  *
SEQ ID NO:35        NAVTSLFEKYKIDPNQIGRLEVGSETVIDKSKSIKTFLMQLFEKCGNTDVEGVDSTNACY
SEQ ID NO:26        TVVNSLLKKYKIDPKLIGRLEVGSETVIDKSKSIKTWLMQIFEESDNTDIEGVDSSNACY
SEQ ID NO:28        TVVTSLLKKYKVDPKLIGRLEVGSETVIDKSKSIKTWLMQIFEECGNTDIEGVDSSNACY
SEQ ID NO:30        TVVSSLLEKYAIDPKQIGRLEVGSETVIDKSKSIKTFIMQIFEKYGNTDIEGVDSTNACY
SEQ ID NO:32        TVVKSLLEKYHIDPKLIGRLEVGSETVIDKSKSIKTWLMQNFEESGNTTLKELTNYHLC-
                    61                                                         120

******* *** ***************************************  ***  ***
SEQ ID NO:35        GGTAALLNCVNWVESNSWDGRYGLVICTDSAVYAEGPARPTGGAAAIAMLIGPDAPIVFE
SEQ ID NO:26        GGTAALLNCVNWVESNSWDGRYGLVVCTDSAVYAEGPARPTGGAAAIAMLIGPNAPIAFE
SEQ ID NO:28        GGTAALLNCVNWVESNSWDGRYGLVVCTDSAVYAEGPARPTGGAAAIAMLIGPNAPIAFE
SEQ ID NO:30        GGTAALFNCVNWVESSSWDGRYGLVVCTDSAVYAEGPARPTGGAAAVAMLIGPDAPISFE
SEQ ID NO:32        -----------------------------------------------------------
                    121                                                        180
```

FIG. 2B

```
                    *  ****** ********************  ** * *  ***
SE3 ID NO:35        SKLRASHMAHVYDFYKPNLASEYPVVDGKLSQTCYLMALDSCYKHLCNKFEKIEGKEFSI
SE3 ID NO:26        SKYRASHMAHVYDFYKPDLASEYPVVDGKLSQTCYLMALDSCYRQFCNKYEKIAGKQFSI
SE3 ID NO:28        SKYKASHMAHVYDFYKPDLASEYPVVDGKLSQTCYLMALDSCYRQFCKKYEKLAGKQFSI
SE3 ID NO:30        SKLRGSHMAHAYDFYKPNLASEYPVVDGKLSQTCYLMALDSCYNHLSHKYEKQEGKQFSI
SE3 ID NO:32        ------------------------------------------------------------
                   181                                                         240

**  *  ********************* ***       *   *********
SE3 ID NO:35        NDADYIVFHSPYNKLVQKSFARLLYNDFLRNASSIDEAAKEKFTPYSSLTLDESYQSRDL
SE3 ID NO:26        SDAEYFVFHSPYNKLVQKSFARLYNDEMRNCSYVDDDVKEKLQSFSNLTGEESYQSRDL
SE3 ID NO:28        SDADYFVFHSPYNKLVQKSFARLYYNDFTRDCSSVDNDAKEKLQPFSNLTGEESYQSRDL
SE3 ID NO:30        SDAEYFVFHSPYNKLVQKSFARLVENDFLKNASFVDEAAKEKLEPFATLSGDESYQSRDL
SE3 ID NO:32        ------------------------------------------------------------
                   241                                                         300

**  *    *  ****  ****  *** ******************* *  *   ****
SE3 ID NO:35        EKVSQQISKPFYDAKVQPTTLIPKEVGNMYTASLYAAFASLIHNKHNDLAGKRVVMFSYG
SE3 ID NO:26        EKASQQVAKHLYGIKVQPTTLLPKQIGNMYTASLYAALASVLYNKHDSLNGQRIVMFSYG
SE3 ID NO:28        EKASQQVAKPLYDIKVQPSTLLPKQIGNMYTASLYAALASVLYNKHASLDDQRIVMFSYG
SE3 ID NO:30        EKASQQVAKPQYDAKVQPTTLIPKQVGNMYTASLYAAFISLIHNKHSTLDGKRVILFSYG
SE3 ID NO:32        ------------------------------------------------------------
                   301                                                         360
```

FIG. 2C

```
                        *  *  *****              *   *   *      *                 *   **********        **********
SE3 ID NO:35            SGSTATMFSLRLNDNKPPFSISNIASVMDVGGKLKARHEYAPEKFVETMKLMEHRYGAKD
SE3 ID NO:26            SGLTSTMFSLRLNNGQHPFSLSNIGSVLGVTEKLQSRHETLPEKFVETLKLMEHRYGAKD
SE3 ID NO:28            SGLTSTMFSLKLNNGQDPFSLSNIASVLNATEKLESRHMTLPEKFVETLKLMEHRYGAKD
SE3 ID NO:30            SGLTSTMFSLLREGQHPFSLSNIDKMMDVAGKLKSRHEFPPEKFVETMKLMEHRYGGKE
SE3 ID NO:32            ------------------------------------------------------------
                        361                                                        420

*  *      *  *** **   *****                *  *****    ***
SE3 ID NO:35            FVTTKEGIIDLLAPGTYYLKEVDSLYRRFYGKK-GEDGSVA----------------NGH
SE3 ID NO:26            FETSSD--TSLLQPGTFYLTKVDSMYRRFYSQKPAEETGGGKTKCCNG-----FANGH
SE3 ID NO:28            FETCKD--TSLLPPGTFYLTRVDSMYRRFYERKADEEIAAAKAKYSNGHATNGYANGH
SE3 ID NO:30            FVTSKD--TSLLSPGTFYLTEVDSMYRRFYAKKTSENGLVT----------------NGH
SE3 ID NO:32            ------------------------------------------------------------
                        421                                                        478
```

MEVALONATE SYNTHESIS ENZYMES

This application is a divisional of U.S. application Ser. No. 10/142,835, filed May 10, 2002, now U.S. Pat. No. 6,916,972, which is a continuation-in-part of U.S. application Ser. No. 09/433,982, filed Nov. 4, 1999, now abandoned, which claims the benefit of U.S. Provisional Application No. 60/107,277, filed Nov. 5, 1998.

FIELD OF THE INVENTION

This invention is in the field of plant molecular biology. More specifically, this invention pertains to nucleic acid fragments encoding enzymes involved in mevalonate synthesis in plants and seeds.

BACKGROUND OF THE INVENTION

The terpenoids constitute the largest family of natural products, and play diverse functional roles in plants as hormones, photosynthetic pigments, electron carriers, mediators of polysaccharide assembly, and structural components of membranes. In addition, many specific terpenoid compounds serve in communication and defense. Some terpenoids, available in relatively large amounts, are important renewable resources and provide a range of commercially useful products. Members of the terpenoid group also include industrially useful polymers and a number of pharmaceuticals and agrochemicals.

The biosynthesis of terpenoids can be divided into four major processes, the first of which involves the conversion of acetyl-coenzyme A (CoA) to the "active isoprene unit", isopentenyl pyroposphate (IPP). By the action of various prenyltransferases this precursor is transformed into higher order terpenoid building blocks, geranyl pyrophosphate (GPP, $C_{10}$), farnesyl pyrophosphate (FPP, $C_{15}$), and geranylgeranyl pyrophosphate (GGPP, $C_{20}$). These branch point intermediates may then self-condense (to the $C_{30}$ and $C_{40}$ precursors of sterols and carotenoids, respectively), be utilized in alkylation reactions to provide prenyl side chains of a range of non-terpenoids, or undergo internal addition to create the basic parental skeletons of the various terpenoid families (McGarvery and Croteau (1995) *Plant Cell* 7:1015–1026).

The initial steps of the pathway involve the fusion of three molecules of acetyl-CoA to produce the C6 compound 3-hydroxy-3-methylglutaryl-CoA (HMG-CoA). The first two reactions are catalyzed by two separate enzymes, acetoacetyl-CoA thiolase and HMG-CoA synthase. Neither of these enzymes has been extensively studied in plants. The next step, catalyzed by HMG-CoA reductase, is of paramount importance in animals as the rate limiting reaction in cholesterol biosynthesis (for review, see Goldstein and Brown (1990) *Nature* 343:425–430). This enzyme catalyzes two reduction steps, each requiring NADPH. Reduced cholesterol synthesis is caused not only by decreased HMG-CoA reductase but also by the coordinate down-regulation of entire pathway of cholesterol biosynthesis (Honda et al. (1998) *J. Lipid Res.* 39:44–50).

The mevalonate resulting from the reduction of HMG-CoA is sequentially phosphorylated by two separate kinases, mevalonate kinase, and phosphomevalonate kinase, to form 5-pyrophosphomevalonate. Formation of IPP is then catalyzed by pyrophosphomevalonate decarboxylase, which performs a concerted decarboxylative elimination. This enzyme requires ATP and a divalent metal ion. The tertiary hydroxyl group of pyrophosphomevalonate is phosphorylated before the concerted elimination, thus making a better leaving group (McGarvery and Croteau (1995) *Plant Cell* 7:1015–1026). IPP is the basic $C_5$ building block that is added to prenyl pyrophosphate cosubstrates to form longer chains. IPP is first isomerized to the allylic ester dimehylallyl pyrophosphate (DMAPP) by IPP isomerase.

Isoprene is synthesized directly from DMAPP by diphosphate elimination in a reaction catalyzed by isoprene synthase. Higher terpenoids are generated by the action of prenyltransferases which perform multistep reactions beginning with DMAPP and IPP to form higher isoprenologs. GPP synthase forms the $C_{10}$ intermediate (GPP) from DMAPP and IPP. This synthase has been characterized in a number of plant species (Croteau and Purkett (1989) *Arch. Biochem. Biophys.* 271:524–535). FPP synthase forms the $C_{15}$ intermediate (FPP) in two discrete steps: first DMPP and IPP form GPP which remains bound to the enzyme; then another IPP is added to yield FPP (McGarvery and Croteau (1995) *Plant Cell* 7:1015–1026).

The enzymes forming the HMG-CoA leading to ketone bodies occur in the mitochondria whereas those responsible for the synthesis of the HMG-CoA that is destined for sterol biosynthesis are located in the cytosol. Their catalytic mechanisms, however, are identical. HMG-CoA reductase has been localized to plastids and mitochondria in radish (Bach (1986) *Lipids* 21:82–88; Bach (1987) *Plant Physiol. Biochem.* 25:163–178) although the *Arabidopsis* enzyme is thought to be localized only to the endoplasmic reticulum (Enjuto et al. (1994) *Proc. Natl. Acad. Sci. USA* 91:927–931). Mevalonate kinase, phosphomevalonate kinase, mevalonate diphosphate decarboxylase, isopentenyl diphosphate isomerase, and farnesyl diphosphate (FPP) synthase are localized predominantly in peroxisomes (Lenka and Skaidrite (1996) *J. Biol. Chem.* 271:1784–1788).

Acetoacetyl-CoA C-acetyltransferase, also called acetoacetyl-CoA thiolase (EC 2.3.1.9), functions as a homotetramer, plays a major role in ketone body metabolism, and catalyzes the first step in the biosynthesis of poly beta-hydroxybutyrate. The gene encoding acetoacetyl-CoA thiolase has been identified in radish, and a sequence encoding a corn acetoacetyl-CoA thiolase is found in the NCBI database having General Identifier No. 5531937. The corn sequence corresponds to the C-terminal half of the radish sequence. EST sequences with similarities to those encoding acetoacetyl-CoA thiolases are found in the NCBI database having General Identifier Nos. 5607829, 6021192, 5607308, 3763023, 426049, 3107208, 2443029, and 5761368.

HMG-CoA synthase (EC 4.1.3.5) condenses acetyl-CoA with acetoacetyl-CoA to form HMG-CoA. Cytosolic HMG-CoA synthase is a highly regulated enzyme involved in isoprenoid biosynthesis and therefore a potential target for cholesterol-lowering drugs (Russ et al. (1992) *Biochim. Biophys. Acta* 1132:329–331). The genes encoding HMG-CoA synthase have been identified in *Arabidopsis thaliana* and *Pinus sylvestris* but not in any crop species. EST sequences with similarities to those encoding HMG-CoA synthases are found in the NCBI database having General Identifier Nos. 5030550, 6012290, 5901402, 3760977, 2427448, 428081, and 454498.

SUMMARY OF THE INVENTION

The present invention concerns an isolated polynucleotide comprising: (a) a first nucleotide sequence encoding a first polypeptide having acetoacetyl-CoA thiolase activity, wherein the amino acid sequence of the first polypeptide and the amino acid sequence of SEQ ID NO:18, 20, 22, or 24 have at least 80%, 85%, 90%, or 95% sequence identity based on the Clustal alignment method, (b) a second nucleotide sequence encoding a second polypeptide having hydroxylmethylglutaryl-CoA synthase activity, wherein the amino acid sequence of the second polypeptide and the amino acid sequence of SEQ ID NO:26, 28, 30, or 32 have at least 80%, 85%, 90%, or 95% sequence identity based on the Clustal alignment method, or (c) the complement of the first or second nucleotide sequence.

In a second embodiment, the first polypeptide preferably comprises the amino acid sequence of SEQ ID NO:18, 20, 22, or 24, and the second polypeptide preferably comprises the amino acid sequence of SEQ ID NO:26, 28, 30, or 32.

In a third embodiment, the first nucleotide sequence preferably comprises the nucleotide sequence of SEQ ID NO:17, 19, 21, 23, and the second nucleotide sequence preferably comprises the nucleotide sequence of SEQ ID NO:25, 27, 29, or 31.

In a fourth embodiment, this invention relates to a vector comprising the polynucleotide of the present invention, or to a chimeric gene comprising the polynucleotide of the present invention operably linked to at least one regulatory sequence. The invention also includes a cell, a plant, or a seed comprising the chimeric gene of the present invention. The cell may be a eukaryotic cell such as a plant cell, or a prokaryotic cell such as a bacterial cell.

In a fifth embodiment, the invention relates to a virus, preferably a baculovirus, comprising an isolated polynucleotide of the present invention or a chimeric gene of the present invention.

In a sixth embodiment, the invention relates to a method of transforming a cell by introducing into the cell a nucleic acid comprising a polynucleotide of the present invention. The invention also concerns a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In a seventh embodiment, the present invention relates to (a) a method for producing a polynucleotide fragment comprising selecting a nucleotide sequence comprised by any of the polynucleotides of the present invention, wherein the selected nucleotide sequence contains at least 30, 40, or 60 nucleotides, and synthesizing a polynucleotide fragment containing the selected nucleotide sequence, and (b) the polynucleotide fragment produced by this method.

In an eighth embodiment, the present invention relates to an isolated polynucleotide fragment comprising a nucleotide sequence comprised by any of the polynucleotides of the present invention, wherein the nucleotide sequence contains at least 30, 40, or 60 nucleotides, and a cell, a plant, and a seed comprising the isolated polynucleotide.

In a ninth embodiment, the present invention concerns an isolated polypeptide having acetoacetyl-CoA thiolase activity, wherein the amino acid sequence of the polypeptide and the amino acid sequence of SEQ ID NO:18, 20, 22, or 24 have at least 80%, 85%, 90%, or 95% identity based on the Clustal alignment method. The isolated polypeptide having acetoacetyl-CoA thiolase activity preferably comprises the amino acid sequence of SEQ ID NO:18, 20, 22, or 24.

In a tenth embodiment, the present invention concerns an isolated polypeptide having hydroxymethyl glutaryl-CoA synthase activity, wherein the amino acid sequence of the polypeptide and the amino acid sequence of SEQ ID NO:26, 28, 30, or 32 have at least 80%, 85%, 90%, or 95% identity based on the Clustal alignment method. The isolated polypeptide having hydroxymethyl glutaryl-CoA synthase activity preferably comprises the amino acid sequence of SEQ ID NO:26, 28, 30, or 32.

In an eleventh embodiment, the invention concerns a method for isolating a polypeptide encoded by the polynucleotide of the present invention comprising isolating the polypeptide from a cell containing a chimeric gene comprising the polynucleotide operably linked to a regulatory sequence.

In a twelfth embodiment, the invention relates to a method of selecting an isolated polynucleotide that affects the level of expression of an acetoacetyl-CoA thiolase or hydroxylmethylglutaryl-CoA synthase polypeptide in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the acetoacetyl-CoA thiolase or hydroxylmethylglutaryl-CoA synthase polypeptide in the host cell containing the isolated polynucleotide or the isolated chimeric gene; and (d) comparing the level of the acetoacetyl-CoA thiolase or hydroxylmethylglutaryl-CoA synthase polypeptide in the host cell containing the isolated polynucleotide or the chimeric gene with the level of the acetoacetyl-CoA thiolase or hydroxylmethylglutaryl-CoA synthase polypeptide in the host cell that does not contain the isolated polynucleotide or the chimeric gene.

In a thirteenth embodiment, the invention concerns a method of obtaining a nucleic acid fragment encoding a substantial portion of an acetoacetyl-CoA thiolase or hydroxylmethylglutaryl-CoA synthase polypeptide, preferably a plant acetoacetyl-CoA thiolase or hydroxylmethylglutaryl-CoA synthase polypeptide, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs:17, 19, 21, 23, 25, 27, 29, and 31 and the complement of such nucleotide sequences; and amplifying a nucleic acid fragment (preferably a cDNA inserted in a cloning vector) using the oligonucleotide primer. The amplified nucleic acid fragment preferably will encode a substantial portion of an acetoacetyl-CoA thiolase or hydroxylmethylglutaryl-CoA synthase amino acid sequence.

In a fourteenth embodiment, this invention relates to a method of obtaining a nucleic acid fragment encoding all or a substantial portion of the amino acid sequence encoding an acetoacetyl-CoA thiolase or hydroxylmethylglutaryl-CoA synthase comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a fifteenth embodiment, this invention concerns a composition, such as a hybridization mixture, comprising an isolated polynucleotide of the present invention.

In a sixteenth embodiment, this invention concerns a method for positive selection of a transformed cell comprising: (a) transforming a host cell with a chimeric gene of the present invention or an expression cassette of the present invention; and (b) growing the transformed host cell, preferably a plant cell, such as a monocot or a dicot, under conditions which allow expression of the acetoacetyl-CoA thiolase or hydroxylmethylglutaryl-CoA synthase in an amount sufficient to complement a null mutant to provide a positive selection means.

In an seventeenth embodiment, this invention relates to a method of altering the level of expression of an acetoacetyl-CoA thiolase or hydroxylmethylglutaryl-CoA synthase polypeptide in a host cell comprising: (a) transforming a host cell with a chimeric gene of the present invention; and (b) growing the transformed host cell under conditions that are suitable for expression of the chimeric gene wherein expression of chimeric gene results in production of altered levels of the acetoacetyl-CoA thiolase or hydroxylmethylglutaryl-CoA synthase polypeptide in the transformed host cell.

In an eighteenth embodiment, this invention concerns a method for evaluating at least one compound for its ability to inhibit acetoacetyl-CoA thiolase or hydroxylmethylglutaryl-CoA synthase activity, comprising the steps of: (a) introducing into a host cell a chimeric gene of the invention; (b) growing the host cell under conditions that are suitable for expression of the chimeric gene wherein expression of the chimeric gene results in production of an acetoacetyl-CoA thiolase or hydroxylmethylglutaryl-CoA synthase; (c) optionally, purifying the acetoacetyl-CoA thiolase or hydroxylmethylglutaryl-CoA synthase expressed in the host cell; (d) treating the acetoacetyl-CoA thiolase or hydroxylmethylglutaryl-CoA synthase with a compound to be tested; (e) comparing the activity of the acetoacetyl-CoA thiolase or hydroxylmethylglutaryl-CoA synthase that has been treated with a test compound to the activity of an untreated acetoacetyl-CoA thiolase or hydroxylmethylglutaryl-CoA synthase, and (f) selecting compounds with potential for inhibitory activity.

As used herein, the following terms shall apply:

"Mevalonate synthesis enzyme" refers to acetoacetyl-CoA thiolase and/or hydroxymethylglutaryl-CoA synthase; and "Polypeptide" refers to an amino acid sequence.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A–1C depict the amino acid sequence alignment between the acetoacetyl-CoA thiolase from corn clone cr1n.pk0112.c7:fis (SEQ ID NO:18), rice clone rlr6.pk0076.c2:fis (SEQ ID NO:20), soybean clone src3c.pk002.d7:fis (SEQ ID NO:22), wheat clone wre1n.pk0044.b2:fis (SEQ ID NO:24), and *Raphanus sativus* (NCBI General Identifier No. 1542941, SEQ ID NO:33) and *Zea mays* (NCBI General Identifier No. 5531937, SEQ ID NO:34) acetoacetyl-CoA thiolases. Amino acids which are conserved among all sequences are indicated with an asterisk (*) above the alignment. Dashes are used by the program to maximize alignment of the sequences. Alignment of amino acids 1 through 180 is shown in FIG. 1A; alignment of amino acids 181 through 360 is shown in FIG. 1B; and alignment of amino acids 361 through 420 is shown in FIG. 1C.

FIGS. 2A–2C depict the amino acid sequence alignment between the hydroxymethylglutaryl-CoA synthase from corn clone chp2.pk0017.b8:fis (SEQ ID NO:26), rice clone rca1c.pk007.f10:fis (SEQ ID NO:28), soybean clone sl1.pk0067.c3:f13 (SEQ ID NO:30), a wheat contig assembled from clones wdk1c.pk012.f13 and wlmk4.pk0017.g7 (SEQ ID NO:32), and *Arabidopsis thaliana* (NCBI General Identifier No. 1708236, SEQ ID NO:35) hydroxymethylglutaryl-CoA synthase. Amino acids which are conserved among all sequences are indicated with an asterisk (*) above the alignment. Dashes are used by the program to maximize alignment of the sequences. Alignment of amino acids 1 through 180 is shown in FIG. 2A; alignment of amino acids 181 through 360 is shown in FIG. 2B; and alignment of amino acids 361 through 478 is shown in FIG. 2C.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Mevalonate Synthesis Enzymes

| Protein | Clone Designation | SEQ ID NO: (Nucleotide) | SEQ ID NO: (Amino Acid) |
|---|---|---|---|
| Corn Acetoacetyl-CoA thiolase | cr1n.pk0112.c7 | 1 | 2 |
| Rice Acetoacetyl-CoA thiolase | rlr6.pk0076.c2 | 3 | 4 |
| Soybean Acetoacetyl-CoA thiolase | src3c.pk002.d7 | 5 | 6 |
| Wheat Acetoacetyl-CoA thiolase | wre1n.pk0044.b2 | 7 | 8 |
| Corn Hydroxymethylglutaryl-CoA synthase | chp2.pk0017.b8 | 9 | 10 |
| Rice Hydroxymethylglutaryl-CoA synthase | rca1c.pk007.f10 | 11 | 12 |
| Soybean Hydroxymethylglutaryl-CoA synthase | sl1.pk0067.c3 | 13 | 14 |
| Wheat Hydroxymethylglutaryl-CoA synthase | wlm12.pk0011.h1 | 15 | 16 |
| Corn Acetoacetyl-CoA thiolase | cr1n.pk0112.c7:fis | 17 | 18 |
| Rice Acetoacetyl-CoA thiolase | rlr6.pk0076.c2:fis | 19 | 20 |
| Soybean Acetoacetyl-CoA thiolase | src3c.pk002.d7:fis | 21 | 22 |
| Wheat Acetoacetyl-CoA thiolase | wre1n.pk0044.b2:fis | 23 | 24 |
| Corn Hydroxymethylglutaryl-CoA synthase | chp2.pk0017.b8:fis | 25 | 26 |
| Rice Hydroxymethylglutaryl-CoA synthase | rca1c.pk007.f10:fis | 27 | 28 |
| Soybean Hydroxymethylglutaryl-CoA synthase | sl1.pk0067.c3:fis | 29 | 30 |
| Wheat Hydroxymethylglutaryl-CoA synthase | Contig of: wdk1c.pk012.f13 wlmk4.pk0017.g7 | 31 | 32 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 60 contiguous nucleotides, preferably at least 40 contiguous nucleotides, most preferably at least 30 contiguous nucleotides, of the nucleic acid sequence of the SEQ ID NOs:1, 3, 5, 7, 9, 11, 13, 15, 17, 19, 21, 23, 25, 27, 29, and 31.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 and the complement of such nucleotide sequences may be used in methods of selecting an isolated polynucleotide that affects the expression of a polypeptide in a host cell. A method of selecting an isolated polynucleotide (such as mevalonate synthesis enzyme) that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several mevalonate synthesis enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other acetoacetyl-CoA thiolases or hydroxymethylglutaryl-CoA synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as acetoacetyl-CoA thiolase or hydroxymethylglutaryl-CoA synthase) preferably a substantial portion of a plant polypeptide of a gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of phytoalexins and/or pigments in those cells. Because these enzymes are involved in mevalonate synthesis, they may be targets for screening of crop protection chemicals.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by altering the coding sequence to encode the instant polypeptides with appropriate intracellular targeting sequences such as transit sequences (Keegstra (1989) *Cell*

56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded mevalonate synthesis enzyme. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze various steps in mevalonate synthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| chp2 | Corn (B73 and MK593) 11 Day Old Leaf Treated 24 Hours With PDO Herbicides* | chp2.pk0017.b8 |
| cr1n | Corn Root From 7 Day Old Seedlings** | cr1n.pk0112.c7 |
| rca1c | Rice Nipponbare callus | rca1c.pk007.f10 |
| rlr6 | Rice Leaf 15 Days After Germination, 6 Hours After Infection of Strain *Magaporthe grisea* 4360-R-62 (AVR2-YAMO); Resistant | rlr6.pk0076.c2 |
| sl1 | Soybean Two-Week-Old Developing Seedlings | sl1.pk0067.c3 |
| src3c | Soybean 8 Day Old Root Infected With Cyst Nematode | src3c.pk002.d7 |
| wdk1c | Wheat Developing Kernel, 3 Days After Anthesis | wdk1c.pk012.f13 |
| wlm12 | Wheat Seedlings 12 Hours After Inoculation With *Erysiphe graminis f.* sp *tritici* | wlm12.pk0011.h1 |
| wlmk4 | Wheat Seedlings 4 Hours After Inoculation With *Erysiphe graminis f.* sp *tritici* and treatment with Herbicide*** | wlmk4.pk0017.g7 |
| wre1n | Wheat Root From 7 Day Old Etiolated Seedling** | wre1n.pk0044.b2 |

*Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference. Application of 2-[(2,3-dihydro-5,8-dimethylspiro[4H-1-benzothiopyran-4,2'-[1,3]dioxolan]-6-yl)carbonyl]-1,3-cyclohexanedione S,S-dioxide; also named 2-[(2,3-dihydro-5,8-dimethylspiro[4H-1-benzothiopyran-4,2'-[1,3]dioxolan]-6-yl)carbonyl]-3-hydroxy-2-cyclohexen-1-one S,S-dioxide; synthesis and methods of using this compound are described in WO 97/01550, incorporated herein by reference.
**These libraries were normalized essentially as described in U.S. Pat. No. 5,482,845, incorporated herein by reference.
***Application of 2-[(2,3-dihydro-5,8-dimethylspiro[4H-1-benzothiopyran-4,2'-[1,3]dioxolan]-6-yl)carbonyl]-1,3-cyclohexanedione S,S-dioxide; also named 2-[(2,3-dihydro-5,8-dimethylspiro[4H-1-benzothiopyran-4,2'-[1,3]dioxolan]-6-yl)carbonyl]-3-hydroxy-2-cyclohexen-1-one S,S-dioxide; synthesis and methods of using this compound are described in WO 97/01550, incorporated herein by reference cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding mevalonate synthesis enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Acetoacetyl-CoA Thiolase

The BLASTX search performed using the EST sequences from the clones listed in Table 3, and included in U.S. Provisional Application No. 60/107,277 filed Nov. 5, 1998, revealed similarity of the polypeptides encoded by the cDNAs to acetoacetyl-CoA thiolase from *Raphanus sativus* (NCBI General Identifier No. 1542941). The BLSTP search using the sequences of the amino acid sequences encoded by the entire cDNA inserts in the indicated clones revealed similarity to acetoacetyl-CoA thiolase from *Arabidopsis thaliana*, *Raphanus sativus*, and *Zea mays* (NCBI General Identifier Nos. 8777413, 1542941 and 5531937). The *Zea mays* sequence, published 20 Jul. 1999, contains 214 amino acids which correspond to the C-terminal half of the radish sequence. Shown in Table 3 are the BLAST results for individual ESTs ("EST"), the sequences of the entire cDNA inserts comprising the indicated cDNA clones ("FIS"), or the FIS sequences encoding the entire protein ("CGS"):

TABLE 3

BLAST Results for Sequences Encoding Polypeptides Homologous to Acetoacetyl-CoA Thiolase

| Clone | Status | NCBI General Identifier No. | BLAST pLog Score |
|---|---|---|---|
| cr1n.pk0112.c7 | EST | 1542941 | 48.15 |
| rlr6.pk0076.c2 | EST | 1542941 | 33.00 |
| src3c.pk002.d7 | EST | 1542941 | 72.15 |
| wre1n.pk0044.b2 | EST | 1542941 | 57.05 |
| cr1n.pk0112.c7:fis | CGS | 1542941 | 176.00 |
|  |  | 8777413 | >180.00 |
| rlr6.pk0076.c2:fis | CGS | 1542941 | 174.00 |
|  |  | 8777413 | >180.00 |
| src3c.pk002.d7:fis | CGS | 1542941 | 254.00 |
|  |  | 8777413 | >180.00 |
| wre1n.pk0044.b2:fis | FIS | 5531937 | 97.70 |

FIGS. 1A–1C present an alignment of the amino acid sequences set forth in SEQ ID NOs:18, 20, 12, and 24 and the *Raphanus sativus* and *Zea mays* sequences (SEQ ID NOs:33 and 34). The data in Table 4 represents a calculation of the percent identity of the amino acid sequences set forth in SEQ ID NOs:2, 4, 6, 8, 18, 20, 12, and 24, the *Raphanus sativus* sequence (NCBI General Identifier No. 1542941), and the *Arabidopsis thaliana* sequence (NCBI General Identifier No. 8777413).

TABLE 4

Percent Identity of Amino Acid Sequences Deduced From the Nucleotide Sequences of cDNA Clones Encoding Polypeptides Homologous to Acetoacetyl-CoA Thiolase

| Clone | SEQ ID NO. | Percent Identity to 1542941 | Percent Identity to 8777413 |
|---|---|---|---|
| cr1n.pk0112.c7 | 2 | 75.4 | 84.2 |
| rlr6.pk0076.c2 | 4 | 79.5 | 80.8 |
| src3c.pk002.d7 | 6 | 81.3 | 86.0 |
| wre1n.pk0044.b2 | 8 | 76.9 | 76.9 |
| cr1n.pk0112.c7:fis | 18 | 75.4 | 79.8 |
| rlr6.pk0076.c2:fis | 20 | 75.4 | 79.8 |
| src3c.pk002.d7:fis | 22 | 81.4 | 84.3 |
| wre1n.pk0044.b2:fis | 24 | 74.0 | 78.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a wheat acetoacetyl-CoA thiolase and entire corn, rice, and soybean acetoacetyl-CoA thiolases. These sequences represent the first entire corn, and the first rice, soybean, and wheat sequences encoding acetoacetyl-CoA thiolase.

Example 4

Characterization of cDNA Clones Encoding Hydroxymethylglutaryl-CoA Synthase

The BLASTX search performed using the EST sequences from the clones listed in Table 5, and included in U.S. Provisional Application No. 60/107,277 filed Nov. 5, 1998, revealed similarity of the polypeptides encoded by the cDNAs to hydroxymethylglutaryl-CoA synthase from *Arabidopsis thaliana* (NCBI General Identifier No. 1708236). The BLSTX search using the sequences of the entire cDNA inserts, or a longer wheat sequence revealed similarity to the same hydroxymethylglutaryl-CoA synthase. Shown in Table 5 are the BLAST results for individual ESTs ("EST"), the contigs assembled from two or more ESTs ("Contig"), or the sequences of the entire cDNA inserts comprising the indicated cDNA clones encoding the entire protein ("CGS"). A BLASTP of the amino acid sequences encoding the entire protein performed in March, 2002 gave a similarity to the hydroxymethylglutaryl-CoA synthase polypeptides from *Hevea brasiliensis* (NCBI General Identifier No. 16417956):

TABLE 5

BLAST Results for Sequences Encoding Polypeptides Homologous to Hydroxymethylglutaryl-CoA Synthase

| Clone | Status | BLAST pLog Score 1708236 | 16417956 |
|---|---|---|---|
| chp2.pk0017.b8 | EST | 71.70 | |
| rca1c.pk007.f10 | EST | 63.52 | |
| sl1.pk0067.c3 | EST | 67.00 | |
| wlm12.pk0011.h1 | EST | 34.00 | |
| chp2.pk0017.b8:fis | CGS | >254.00 | >180.00 |
| rca1c.pk007.f10:fis | CGS | >254.00 | >180.00 |
| sl1.pk0067.c3:fis | CGS | >254.00 | |
| Contig of: wdk1c.pk012.f13 wlmk4.pk0017.g7 | Contig | 52.70 | |

FIGS. 2A–2C present an alignment of the amino acid sequences set forth in SEQ ID NOs:26, 28, 30, and 32 and the *Arabidopsis thaliana* sequence (SEQ ID NO:35). The data in Table 6 presents a calculation of the percent identity of the amino acid sequences set forth in SEQ ID NOs:10, 12, 14, 16, 26, 28, 30, and 32, the *Arabidopsis thaliana* sequence (NCBI General Identifier No. 1708236) and the *Hevea brasiliensis* sequence (NCBI General Identifier No. 16417956).

TABLE 6

Percent Identity of Amino Acid Sequences Deduced From the Nucleotide Sequences of cDNA Clones Encoding Polypeptides Homologous to Hydroxymethylglutaryl-CoA Synthase

| Clone | SEQ ID NO. | Percent Identity to 1708236 | 16417956 |
|---|---|---|---|
| chp2.pk0017.b8 | 10 | 84.6 | 87.7 |
| rca1c.pk007.f10 | 12 | 80.3 | 82.0 |
| sl1.pk0067.c3 | 14 | 83.7 | 88.6 |
| wlm12.pk0011.h1 | 16 | 68.6 | 74.3 |
| chp2.pk0017.b8:fis | 26 | 75.1 | 78.2 |
| rca1c.pk007.f10:fis | 28 | 75.3 | 77.3 |
| sl1.pk0067.c3:fis | 30 | 79.8 | 85.9 |

TABLE 6-continued

Percent Identity of Amino Acid Sequences Deduced From the Nucleotide Sequences of cDNA Clones Encoding Polypeptides Homologous to Hydroxymethylglutaryl-CoA Synthase

| Clone | SEQ ID NO. | Percent Identity to 1708236 | 16417956 |
|---|---|---|---|
| Contig of: wdk1c.pk012.f13 wlmk4.pk0017.g7 | 32 | 75.7 | 78.3 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a wheat hydroxymethylglutaryl-CoA synthase and entire corn, rice, and soybean hydroxymethylglutaryl-CoA synthase. These sequences represent the first monocot and soybean sequences encoding hydroxymethylglutaryl-CoA synthase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian *Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the $^{35}$S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the $^{35}$S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Mevalonate Synthesis Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the enzymes involved in mevalonate synthesis disclosed herein. Assays may be conducted under well known experimental conditions which permit optimal enzymatic activity. For example, assays for acetoacetyl-CoA thiolase are presented by Watanabe et al. (1998) *Tohoku J. Exp. Med.* 184:29–38). Assays for HMG-CoA synthase are presented by (Scharnagl et al. (1995) *J. Lipid Res.* 36:622–627).

What is claimed is:

1. An isolated polynucleotide comprising:
   (a) a nucleotide sequence encoding a polypeptide having HMG-CoA synthase activity, wherein the amino acid sequence of the polypeptide and the amino acid sequence of SEQ ID NO:30 have at least 90% sequence identity based on the Clustal alignment method, or
   (b) the full complement of the nucleotide sequence.

2. The polynucleotide of claim 1, wherein the sequence identity is at least 95%.

3. The polynucleotide of claim 1, wherein the polypeptide comprises SEQ ID NO: 30.

4. The polynucleotide of claim 1, wherein the nucleotide sequence comprises SEQ ID NO: 29.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. The cell of claim 8, wherein the cell is selected from the group consisting of a yeast cell, a bacterial cell and a plant cell.

10. A method for producing a plant comprising transforming a plant cell with the polynucleotide of claim 1 and regenerating a plant from the transformed plant cell.

11. A plant comprising the recombinant DNA construct of claim 6.

12. A seed comprising the recombinant DNA construct of claim 6.

13. A virus comprising the polynucleotide of claim 1.

* * * * *

SEQUENCE LISTING

<160> NUMBER OF SEQ ID NOS: 35

<210> SEQ ID NO 1
<211> LENGTH: 471
<212> TYPE: DNA
<213> ORGANISM: Zea mays
<220> FEATURE:
<221> NAME/KEY: unsure
<222> LOCATION: (8)
<223> OTHER INFORMATION: n = A, C, G, or T

<400> SEQUENCE: 1

```
ctcgtgcncg cgcacacact gtctttctct gcctttcttt ccctagcgcc gcgccggccc      60
gccattcgat caggccgctt cgccggcgac agcatattcc aggtcggttg gttttggcac     120
ttcggaccgg cggccatggc ttccgacggc atcggcccca gagatgtatg tgttgttggg     180
gttgcacgca ccccaatggg cggtttcctt ggtgccttgt ctcccttgcc tgctacgaaa     240
cttggctcta tagtaattca agctgctctg gaaagagcaa acgtggatcc agccctcgtg     300
caggaggtct actttggaaa cgtcttgagt gctaatttgg ggcaagctcc tgcaaggcaa     360
gctgctctgg gtgccgggat accaaactct gttgtttgca ccactgttaa caaagtctgt     420
gcatctggca tgaaagctac tatgtttgca gcacagtcaa ttcaattggg t              471
```

<210> SEQ ID NO 2
<211> LENGTH: 114
<212> TYPE: PRT
<213> ORGANISM: Zea mays

<400> SEQUENCE: 2

```
Ala Ala Met Ala Ser Asp Gly Ile Gly Pro Arg Asp Val Cys Val Val
  1               5                  10                  15

Gly Val Ala Arg Thr Pro Met Gly Gly Phe Leu Gly Ala Leu Ser Pro
             20                  25                  30

Leu Pro Ala Thr Lys Leu Gly Ser Ile Val Ile Gln Ala Ala Leu Glu
         35                  40                  45

Arg Ala Asn Val Asp Pro Ala Leu Val Gln Glu Val Tyr Phe Gly Asn
     50                  55                  60

Val Leu Ser Ala Asn Leu Gly Gln Ala Pro Ala Arg Gln Ala Ala Leu
 65                  70                  75                  80
```

Gly Ala Gly Ile Pro Asn Ser Val Val Cys Thr Thr Val Asn Lys Val
                85                  90                  95

Cys Ala Ser Gly Met Lys Ala Thr Met Phe Ala Ala Gln Ser Ile Gln
            100                 105                 110

Leu Gly

<210> SEQ ID NO 3
<211> LENGTH: 606
<212> TYPE: DNA
<213> ORGANISM: Oryza sativa
<220> FEATURE:
<221> NAME/KEY: unsure
<222> LOCATION: (10)..(11)
<223> OTHER INFORMATION: n = A, C, G, or T
<220> FEATURE:
<221> NAME/KEY: unsure
<222> LOCATION: (27)
<223> OTHER INFORMATION: n = A, C, G, or T
<220> FEATURE:
<221> NAME/KEY: unsure
<222> LOCATION: (31)
<223> OTHER INFORMATION: n = A, C, G, or T
<220> FEATURE:
<221> NAME/KEY: unsure
<222> LOCATION: (42)
<223> OTHER INFORMATION: n = A, C, G, or T
<220> FEATURE:
<221> NAME/KEY: unsure
<222> LOCATION: (59)
<223> OTHER INFORMATION: n = A, C, G, or T
<220> FEATURE:
<221> NAME/KEY: unsure
<222> LOCATION: (92)
<223> OTHER INFORMATION: n = A, C, G, or T
<220> FEATURE:
<221> NAME/KEY: unsure
<222> LOCATION: (99)
<223> OTHER INFORMATION: n = A, C, G, or T
<220> FEATURE:
<221> NAME/KEY: unsure
<222> LOCATION: (147)
<223> OTHER INFORMATION: n = A, C, G, or T
<220> FEATURE:
<221> NAME/KEY: unsure
<222> LOCATION: (159)
<223> OTHER INFORMATION: n = A, C, G, or T
<220> FEATURE:
<221> NAME/KEY: unsure
<222> LOCATION: (164)
<223> OTHER INFORMATION: n = A, C, G, or T
<220> FEATURE:
<221> NAME/KEY: unsure
<222> LOCATION: (221)
<223> OTHER INFORMATION: n = A, C, G, or T

<400> SEQUENCE: 3
tccctacacn nacatacacc ctacaanact ntcactgcca cnaggcgaat cataacacna      60
ccgctccgtg tctgaactac ttcaataacg tnctagttnc ctaaacgcct actcgagttc     120
gaggacttaa taaatggtaa cggcccntga acgtatgna ttcnagaaac gattacgacc     180
gaacccagaa gaagcacaac taatgatact ttaattactt ngaaaagtcg acaacgtgaa     240
cgtttagttt tcgaagaacc ttaaggaagt cttttttaat tacatgtacc tcctcgacac     300
agaaatcctg taggagaacc tacgtcacca cgagcttaaa accagtggga cgaaccacaa     360
gaatccctct ttccaccgtt ttagcctcaa cgaccacaaa cgttaccgcc tccgcctcgt     420
agacgagagc aagagctcga acgtattctt cggaacacta ggtagaggtc aagaggtcct     480
gcaaacacat gagatcaaat aaactaaaag acgaaatcga caaacctgta agaaaataga     540

```
attattaacc cattatttca cacaaacacc acggttttt tttttttttt tttttttttt      600
tttttg                                                                606
```

<210> SEQ ID NO 4
<211> LENGTH: 73
<212> TYPE: PRT
<213> ORGANISM: Oryza sativa

<400> SEQUENCE: 4

```
Phe Ser Ala Val Ala Leu Ala Asn Gln Lys Leu Leu Gly Ile Pro Ser
 1               5                  10                  15

Glu Lys Ile Asn Val His Gly Gly Ala Val Ser Leu Gly His Pro Leu
            20                  25                  30

Gly Cys Ser Gly Ala Arg Ile Leu Val Thr Leu Leu Gly Val Leu Arg
        35                  40                  45

Glu Lys Gly Gly Lys Ile Gly Val Ala Gly Val Cys Asn Gly Gly Gly
    50                  55                  60

Gly Ala Ser Ala Leu Val Leu Glu Leu
65                  70
```

<210> SEQ ID NO 5
<211> LENGTH: 498
<212> TYPE: DNA
<213> ORGANISM: Glycine max
<220> FEATURE:
<221> NAME/KEY: unsure
<222> LOCATION: (472)
<223> OTHER INFORMATION: n = A, C, G, or T

<400> SEQUENCE: 5

```
tctctctctt tttcgcctca ttccatttc atctatcaat ggctccagta gcagcagcat       60
cttcagattc aatcaagcca agagatgttt gcatcgttgg tgttgcacgt acaccaatgg     120
gtggatttct tggtactctg tcatctctat ctgccaccaa gctaggctct atagctattg     180
aagctgctct taaaagggcc aatgttgatc catcccttgt ggaagaagta ttttttggga     240
atgttcttag tgctaatttg gggcaagctc ctgcaagaca agctgctctt ggagcaggaa     300
tatccaattc agttatctgc actaccgtta acaaagtttg tgcatcagga atgaaagctg     360
caatgcttgc tgcacagagt attcaattag cacaaatga tgttgttgtg gctggtggta     420
tggaaagcat gtctaatgta cccaagtacc tggctgaagc aaggaaagga tnacgccttg     480
gacatgattc acttgttg                                                   498
```

<210> SEQ ID NO 6
<211> LENGTH: 150
<212> TYPE: PRT
<213> ORGANISM: Glycine max
<220> FEATURE:
<221> NAME/KEY: UNSURE
<222> LOCATION: (142)
<223> OTHER INFORMATION: Xaa = ANY AMINO ACID

<400> SEQUENCE: 6

```
Val Ala Ala Ala Ser Ser Asp Ser Ile Lys Pro Arg Asp Val Cys Ile
 1               5                  10                  15

Val Gly Val Ala Arg Thr Pro Met Gly Gly Phe Leu Gly Thr Leu Ser
            20                  25                  30

Ser Leu Ser Ala Thr Lys Leu Gly Ser Ile Ala Ile Glu Ala Ala Leu
        35                  40                  45

Lys Arg Ala Asn Val Asp Pro Ser Leu Val Glu Glu Val Phe Phe Gly
```

```
                50                   55                   60
Asn Val Leu Ser Ala Asn Leu Gly Gln Ala Pro Ala Arg Gln Ala Ala
 65                   70                   75                   80

Leu Gly Ala Gly Ile Ser Asn Ser Val Ile Cys Thr Thr Val Asn Lys
                 85                   90                   95

Val Cys Ala Ser Gly Met Lys Ala Ala Met Leu Ala Ala Gln Ser Ile
                100                  105                  110

Gln Leu Gly Thr Asn Asp Val Val Ala Gly Gly Met Glu Ser Met
            115                  120                  125

Ser Asn Val Pro Lys Tyr Leu Ala Glu Ala Arg Lys Gly Xaa Arg Leu
            130                  135                  140

Gly His Asp Ser Leu Val
145                 150

<210> SEQ ID NO 7
<211> LENGTH: 548
<212> TYPE: DNA
<213> ORGANISM: Triticum aestivum
<220> FEATURE:
<221> NAME/KEY: unsure
<222> LOCATION: (364)
<223> OTHER INFORMATION: n = A, C, G, or T
<220> FEATURE:
<221> NAME/KEY: unsure
<222> LOCATION: (490)
<223> OTHER INFORMATION: n = A, C, G, or T

<400> SEQUENCE: 7
attcaaagta atgagcgtgg aattgctgct cgtgacagtg gtgcttttgc atgggagatt      60
gttccgattg aagttcctgt tggtagaggg aaacctgcag tacttgttga caaagatgag    120
agcctagaca agtttgacgc agccaagctg aagaagttac gaccagcatt caaggagaat    180
gctggtactg ttactgctgg aaatgcttct agtataagtg atggtgctgc agcattagta    240
ttggtgagtg ggaagaaggc tcaagaactt ggattgcaag tccttgcaag gattaaggga    300
tttgccgatg cagcccaagc tcctgaacta tttaccacta ccccagcact tgccataccg    360
aagntctcac aaatgctggc tagatcctct cgtattgatt ttatgaaaca atgaaccttc    420
ggctgttcac ttgcaaatca aaactccgga atcctcagaa aagataaatt catggaggac    480
tgtacttagn caccactggg tgcatggtgc ccattggcac ctctcgtgtc taaggagaga    540
tgcagatg                                                             548

<210> SEQ ID NO 8
<211> LENGTH: 121
<212> TYPE: PRT
<213> ORGANISM: Triticum aestivum

<400> SEQUENCE: 8

Ile Gln Ser Asn Glu Arg Gly Ile Ala Ala Arg Asp Ser Gly Ala Phe
  1               5                   10                  15

Ala Trp Glu Ile Val Pro Ile Glu Val Pro Val Gly Arg Gly Lys Pro
                 20                  25                  30

Ala Val Leu Val Asp Lys Asp Glu Ser Leu Asp Lys Phe Asp Ala Ala
             35                  40                  45

Lys Leu Lys Lys Leu Arg Pro Ala Phe Lys Glu Asn Ala Gly Thr Val
 50                  55                  60

Thr Ala Gly Asn Ala Ser Ser Ile Ser Asp Gly Ala Ala Ala Leu Val
 65                  70                  75                  80
```

```
Leu Val Ser Gly Lys Lys Ala Gln Glu Leu Gly Leu Gln Val Leu Ala
             85                  90                  95

Arg Ile Lys Gly Phe Ala Asp Ala Ala Gln Ala Pro Glu Leu Phe Thr
            100                 105                 110

Thr Thr Pro Ala Leu Ala Ile Pro Lys
        115                 120

<210> SEQ ID NO 9
<211> LENGTH: 545
<212> TYPE: DNA
<213> ORGANISM: Zea mays

<400> SEQUENCE: 9
ggtaacccag agtccgacgc acgcctaggg ctcctggaca cagcagagcc cacgccttga      60
ctcgctccgt tcgagtggag cgcacaggca ccggccggcg accagagagg gagcggatcg     120
agggggctcg gcttgagtgg aggagatgga ccgcaaggat gtcgggatcc tcgccatgga     180
catctacttc ccgccctcct gcgtgcagca ggaagcactt gaggcccatg atgggcgag      240 caaagggaag tacaccattg gcttgggca agattgcatg gcctttgca gcgaggtgga      300 ggatgtcatc tcaatgagtt tgacggttgt caattctctg ctgaaaaaat acaagattga     360
tcccaagcta attggtcgct tggaggtggg aagtgaaaca gttatagaca aaagcaaatc     420
catcaaaact tggctgatgc agattttga ggaaagtgat aatactgaca ttgaaggtgt      480
tgactccagc aatgcatgtt atggtgggac agcagcccta ctgaattgtg tgaattgggt     540
cgaaa                                                                  545

<210> SEQ ID NO 10
<211> LENGTH: 130
<212> TYPE: PRT
<213> ORGANISM: Zea mays

<400> SEQUENCE: 10

Lys Asp Val Gly Ile Leu Ala Met Asp Ile Tyr Phe Pro Pro Ser Cys
  1               5                  10                  15

Val Gln Gln Glu Ala Leu Glu Ala His Asp Gly Ala Ser Lys Gly Lys
             20                  25                  30

Tyr Thr Ile Gly Leu Gly Gln Asp Cys Met Ala Phe Cys Ser Glu Val
         35                  40                  45

Glu Asp Val Ile Ser Met Ser Leu Thr Val Val Asn Ser Leu Leu Lys
     50                  55                  60

Lys Tyr Lys Ile Asp Pro Lys Leu Ile Gly Arg Leu Glu Val Gly Ser
 65                  70                  75                  80

Glu Thr Val Ile Asp Lys Ser Lys Ser Ile Lys Thr Trp Leu Met Gln
             85                  90                  95

Ile Phe Glu Glu Ser Asp Asn Thr Asp Ile Glu Gly Val Asp Ser Ser
            100                 105                 110

Asn Ala Cys Tyr Gly Gly Thr Ala Ala Leu Leu Asn Cys Val Asn Trp
        115                 120                 125

Val Glu
    130

<210> SEQ ID NO 11
<211> LENGTH: 508
<212> TYPE: DNA
<213> ORGANISM: Oryza sativa
<220> FEATURE:
<221> NAME/KEY: unsure
```

```
<222> LOCATION: (365)
<223> OTHER INFORMATION: n = A, C, G, or T
<220> FEATURE:
<221> NAME/KEY: unsure
<222> LOCATION: (372)
<223> OTHER INFORMATION: n = A, C, G, or T
<220> FEATURE:
<221> NAME/KEY: unsure
<222> LOCATION: (374)
<223> OTHER INFORMATION: n = A, C, G, or T
<220> FEATURE:
<221> NAME/KEY: unsure
<222> LOCATION: (440)
<223> OTHER INFORMATION: n = A, C, G, or T

<400> SEQUENCE: 11
ctctgctcta gcgtgggcgg agaacacgag gcgtggccgc gtcgtcgtcg gaggagggag      60
cagagatgga cggccgcaag gatgtcggga tcctcgccat ggatatctac ttcccgccca     120
cctgcgtcct ccaggaatcg ctcgaggctc atgacggcgc cagcaaaggg aagtacacca     180
ttggtctcgg ccaagattgc atggccttct gcagtgaggt ggaggatgtc atctcgatga     240
gcatgacagt tgtcacatcc ctgctgaaaa aatacaaggt cgatccaaag ctgattggtc     300
gattggaggt tggcagtgag acagtcatag acaagagcaa atccatcaag acttggctga     360
tgcanatttt cnangaatgc ggtaatactg acatttgaaa ggagttgatt ccaataacgc     420
gtgttatggg gggacaacan cgctgtttga attgtgtgaa actgggttaa aagtaactcc     480
tgggatggac ccaagggcct tgttgttt                                       508

<210> SEQ ID NO 12
<211> LENGTH: 122
<212> TYPE: PRT
<213> ORGANISM: Oryza sativa
<220> FEATURE:
<221> NAME/KEY: UNSURE
<222> LOCATION: (96)
<223> OTHER INFORMATION: Xaa = ANY AMINO ACID
<220> FEATURE:
<221> NAME/KEY: UNSURE
<222> LOCATION: (99)
<223> OTHER INFORMATION: Xaa = ANY AMINO ACID
<220> FEATURE:
<221> NAME/KEY: UNSURE
<222> LOCATION: (121)
<223> OTHER INFORMATION: Xaa = ANY AMINO ACID

<400> SEQUENCE: 12

Lys Asp Val Gly Ile Leu Ala Met Asp Ile Tyr Phe Pro Pro Thr Cys
  1               5                  10                  15

Val Leu Gln Glu Ser Leu Glu Ala His Asp Gly Ala Ser Lys Gly Lys
             20                  25                  30

Tyr Thr Ile Gly Leu Gly Gln Asp Cys Met Ala Phe Cys Ser Glu Val
         35                  40                  45

Glu Asp Val Ile Ser Met Ser Met Thr Val Val Thr Ser Leu Leu Lys
     50                  55                  60

Lys Tyr Lys Val Asp Pro Lys Leu Ile Gly Arg Leu Glu Val Gly Ser
 65                  70                  75                  80

Glu Thr Val Ile Asp Lys Ser Lys Ser Ile Lys Thr Trp Leu Met Xaa
                 85                  90                  95

Ile Phe Xaa Glu Cys Gly Asn Thr Asp Leu Lys Gly Val Asp Ser Asn
            100                 105                 110

Asn Ala Cys Tyr Gly Gly Thr Thr Xaa Leu
        115                 120
```

```
<210> SEQ ID NO 13
<211> LENGTH: 542
<212> TYPE: DNA
<213> ORGANISM: Glycine max
<220> FEATURE:
<221> NAME/KEY: unsure
<222> LOCATION: (346)
<223> OTHER INFORMATION: n = A, C, G, or T
<220> FEATURE:
<221> NAME/KEY: unsure
<222> LOCATION: (444)
<223> OTHER INFORMATION: n = A, C, G, or T
<220> FEATURE:
<221> NAME/KEY: unsure
<222> LOCATION: (457)
<223> OTHER INFORMATION: n = A, C, G, or T
<220> FEATURE:
<221> NAME/KEY: unsure
<222> LOCATION: (529)
<223> OTHER INFORMATION: n = A, C, G, or T

<400> SEQUENCE: 13
tcaaaatcac ataaggtcct cgctgctgct aagtgcctcc ttcttcctcc tatatatata    60
tatatataca tatatgcacg taaagcctct tcgcacaact taaccctctc tctctgagat   120
ggcaaagaat gtggggattc tcgctatcga catctacttc cctcccacct gtattcagca   180
ggaattgctg gaggctcatg atggtgccag taaagggaaa tatactattg gacttggtca   240
agattgcatg gcgttttgta cagaagtaga agatgtcatc tcgatgagtt tgacagtagt   300
ttcttccctt cttgaaaagt atgcgattga tcctaaacaa attggncgtc tggaagtagg   360
cagtgagact gtgattgaca aaagaaatcc atcaaaactt tcatcatgca aatctttgag   420
aaatatggaa ataccgatat tganggcgtt gattcancta atgcatgcta tggaggaact   480
gctgcttggt caatgggtca attgggtgga gagcagctca agggatggnc gctatggact   540
tg                                                                  542

<210> SEQ ID NO 14
<211> LENGTH: 123
<212> TYPE: PRT
<213> ORGANISM: Glycine max
<220> FEATURE:
<221> NAME/KEY: UNSURE
<222> LOCATION: (109)
<223> OTHER INFORMATION: Xaa = ANY AMINO ACID
<220> FEATURE:
<221> NAME/KEY: UNSURE
<222> LOCATION: (114)
<223> OTHER INFORMATION: Xaa = ANY AMINO ACID

<400> SEQUENCE: 14

Met Ala Lys Asn Val Gly Ile Leu Ala Ile Asp Ile Tyr Phe Pro Pro
  1               5                  10                  15

Thr Cys Ile Gln Gln Glu Leu Leu Glu Ala His Asp Gly Ala Ser Lys
                 20                  25                  30

Gly Lys Tyr Thr Ile Gly Leu Gly Gln Asp Cys Met Ala Phe Cys Thr
             35                  40                  45

Glu Val Glu Asp Val Ile Ser Met Ser Leu Thr Val Ser Ser Leu
         50                  55                  60

Leu Glu Lys Tyr Ala Ile Asp Pro Lys Gln Ile Gly Arg Leu Glu Val
 65                  70                  75                  80

Gly Ser Glu Thr Val Ile Asp Gln Lys Lys Ser Ile Lys Thr Phe Ile
                 85                  90                  95

Met Gln Ile Phe Glu Lys Tyr Gly Asn Thr Asp Ile Xaa Gly Val Asp
```

```
                    100                 105                 110
Ser Xaa Asn Ala Cys Tyr Gly Gly Thr Ala Ala
        115                 120
```

<210> SEQ ID NO 15
<211> LENGTH: 561
<212> TYPE: DNA
<213> ORGANISM: Triticum aestivum
<220> FEATURE:
<221> NAME/KEY: unsure
<222> LOCATION: (25)
<223> OTHER INFORMATION: n = A, C, G, or T
<220> FEATURE:
<221> NAME/KEY: unsure
<222> LOCATION: (186)
<223> OTHER INFORMATION: n = A, C, G, or T
<220> FEATURE:
<221> NAME/KEY: unsure
<222> LOCATION: (219)
<223> OTHER INFORMATION: n = A, C, G, or T
<220> FEATURE:
<221> NAME/KEY: unsure
<222> LOCATION: (253)
<223> OTHER INFORMATION: n = A, C, G, or T
<220> FEATURE:
<221> NAME/KEY: unsure
<222> LOCATION: (283)
<223> OTHER INFORMATION: n = A, C, G, or T
<220> FEATURE:
<221> NAME/KEY: unsure
<222> LOCATION: (298)
<223> OTHER INFORMATION: n = A, C, G, or T
<220> FEATURE:
<221> NAME/KEY: unsure
<222> LOCATION: (318)
<223> OTHER INFORMATION: n = A, C, G, or T
<220> FEATURE:
<221> NAME/KEY: unsure
<222> LOCATION: (330)
<223> OTHER INFORMATION: n = A, C, G, or T
<220> FEATURE:
<221> NAME/KEY: unsure
<222> LOCATION: (368)
<223> OTHER INFORMATION: n = A, C, G, or T
<220> FEATURE:
<221> NAME/KEY: unsure
<222> LOCATION: (374)
<223> OTHER INFORMATION: n = A, C, G, or T
<220> FEATURE:
<221> NAME/KEY: unsure
<222> LOCATION: (378)
<223> OTHER INFORMATION: n = A, C, G, or T
<220> FEATURE:
<221> NAME/KEY: unsure
<222> LOCATION: (396)
<223> OTHER INFORMATION: n = A, C, G, or T
<220> FEATURE:
<221> NAME/KEY: unsure
<222> LOCATION: (405)
<223> OTHER INFORMATION: n = A, C, G, or T
<220> FEATURE:
<221> NAME/KEY: unsure
<222> LOCATION: (411)
<223> OTHER INFORMATION: n = A, C, G, or T
<220> FEATURE:
<221> NAME/KEY: unsure
<222> LOCATION: (420)
<223> OTHER INFORMATION: n = A, C, G, or T
<220> FEATURE:
<221> NAME/KEY: unsure
<222> LOCATION: (435)
<223> OTHER INFORMATION: n = A, C, G, or T
<220> FEATURE:
<221> NAME/KEY: unsure
<222> LOCATION: (438)
<223> OTHER INFORMATION: n = A, C, G, or T
<220> FEATURE:

```
<221> NAME/KEY: unsure
<222> LOCATION: (485)
<223> OTHER INFORMATION: n = A, C, G, or T
<220> FEATURE:
<221> NAME/KEY: unsure
<222> LOCATION: (530)
<223> OTHER INFORMATION: n = A, C, G, or T

<400> SEQUENCE: 15
ccccgacgtg ctccgcgtcc acggngctgc caaagtcaca cgaactctct cacgtcacac      60
acgcctcctc ctgcgagcca gccactggga gagcccgcgg aagcacagag cgggaggagg     120
gatcgcgaga tggagtgcaa ggatgtcggg atcctcgcca tggacatgta tttccctccc     180
acctgngtcc agcaggaagc gctggaggtt catgacgggn ccagcaaggg gaagtacaca     240
attgagtctt ggncaagatt gtatggcctt ctgcagcgag gtngaagatg tcatctcnat     300
gagcttgaca gttgtcanat ccctgctggn aaagtaccac atagattcgt gactaattgg     360
tcgcctgnag gttngtancg acacagtgat agacanagta actcnatcag nacgtggctn     420
atgcacaatt ttganganag tggtaacact gacattgagg aattgaccca ataaccattt     480
atggnggaca actgcctgtt aatggtaatt ggtcaaatcg atctggatgn ccaaggctgt     540
ggccgctagt atcggttcca t                                                561

<210> SEQ ID NO 16
<211> LENGTH: 70
<212> TYPE: PRT
<213> ORGANISM: Triticum aestivum
<220> FEATURE:
<221> NAME/KEY: UNSURE
<222> LOCATION: (16)
<223> OTHER INFORMATION: Xaa = ANY AMINO ACID
<220> FEATURE:
<221> NAME/KEY: UNSURE
<222> LOCATION: (60)
<223> OTHER INFORMATION: Xaa = ANY AMINO ACID
<220> FEATURE:
<221> NAME/KEY: UNSURE
<222> LOCATION: (64)
<223> OTHER INFORMATION: Xaa = ANY AMINO ACID

<400> SEQUENCE: 16

Lys Asp Val Gly Ile Leu Ala Met Asp Met Tyr Phe Pro Pro Thr Xaa
  1               5                  10                  15

Val Gln Gln Glu Ala Leu Glu Val His Asp Gly Ala Ala Arg Gly Ser
             20                  25                  30

Thr Gln Leu Ser Leu Gly Gln Asp Cys Met Ala Phe Cys Ser Glu Val
         35                  40                  45

Glu Asp Val Ile Ser Met Ser Leu Thr Val Val Xaa Ser Leu Leu Xaa
     50                  55                  60

Lys Tyr His Ile Asp Ser
 65                  70

<210> SEQ ID NO 17
<211> LENGTH: 1592
<212> TYPE: DNA
<213> ORGANISM: Zea mays

<400> SEQUENCE: 17
gcacgagctc gtgccgcgcg cacacactgt ctttctctgc ctttctttcc ctagcgccgc      60
gccggcgccg ccattcgatc aggccgcttc gccggcgaca gcatattcca ggtcggttgg     120
ttttggcact tcggaccggc ggccatggct tccgacggca tcggcccag agatgtatgt      180
```

```
gttgttgggg ttgcacgcac cccaatgggc ggtttccttg gtgccttgtc tcccttgcct      240
gctacgaaac ttggctctat agtaattcaa gctgctctgg aaagagcaaa cgtggatcca      300
gccctcgtgc aggaggtcta ctttggaaac gtcttgagtg ctaatttggg gcaagctcct      360
gcaaggcaag ctgctctggg tgccgggata ccaaactctg ttgtttgcac cactgttaac      420
aaagtctgtg catctggcat gaaagctact atgtttgcag cacagtcaat tcaattgggt      480
atcaatgata ttgttgtggc tggtggcatg gaaagcatgt ccaatgcccc aaagtacatt      540
gctgaagcta ggaaggggtc tcgttttggt catgacacac ttgttgatgc catgcttaag      600
gatgggcttt gggatgtata caatgattgt gccatgggaa tgtgtgccga gctttgtgct      660
gacaaccatg ccctcacaag agaagaccag gatgcatttg ctatccaaag caacgagcgt      720
ggaattgctg ctcgtgacag tggtgctttt gcatgggaga ttattccggt tcaagttcct      780
gttggtagag gaaaacccccc aacattaatt gagagagatg aaagcctgga taagtttgac      840
ccagtaaaac taaagaaact tcgcccaagt ttcaaggaga atggtggtac agttacagct      900
ggaaatgctt ctagtataag tgatggagct gctgcattag ttttagtgag tgggcagaag      960
gctcaagagc ttggccttca agtccttgca aggatcaaag gttatgctga tgcagctcaa     1020
gctccggagc ttttttacaac cactccagca cttgcaatac caaaggctat cgcaaatgct     1080
ggattagagt catcccgtgt tgatttctat gagattaatg aagcctttttc ggctgttgcg     1140
cttgcaaatc aaaaacttct tggaattcct tcagaaaaga ttaatgttca tggaggagct     1200
gtatccttag gacatcctct cggtgcagt ggtgctcgca ttttggttac ccttattggt     1260
gttctcaggg cgaagagtgg caagatcgga gttgctggtg tctgcaacgg tggaggcgga     1320
gcatcagctc ttgttctgga gctcgcataa gaaatctaga ccttgtagtt agcaaaagct     1380
ccctgaggtg atcttgtagt cttatttttcc gttgtagtag tcccatagaa catttcttaa     1440
tttaatttgg caataaagca aaagctcccct gaggagatat tgcttctgtt ggttgcatag     1500
tagagtatca tgtaataaga gctacagaaa tatttttgat atatttgtga ggatactaca     1560
gaaatatttt atataaaaaa aaaaaaaaaa aa                                    1592
```

<210> SEQ ID NO 18
<211> LENGTH: 401
<212> TYPE: PRT
<213> ORGANISM: Zea mays

<400> SEQUENCE: 18

Met Ala Ser Asp Gly Ile Gly Pro Arg Asp Val Cys Val Val Gly Val
1               5                   10                  15

Ala Arg Thr Pro Met Gly Gly Phe Leu Gly Ala Leu Ser Pro Leu Pro
                20                  25                  30

Ala Thr Lys Leu Gly Ser Ile Val Ile Gln Ala Ala Leu Glu Arg Ala
            35                  40                  45

Asn Val Asp Pro Ala Leu Val Gln Glu Val Tyr Phe Gly Asn Val Leu
        50                  55                  60

Ser Ala Asn Leu Gly Gln Ala Pro Ala Arg Gln Ala Ala Leu Gly Ala
65                  70                  75                  80

Gly Ile Pro Asn Ser Val Val Cys Thr Thr Val Asn Lys Val Cys Ala
                85                  90                  95

Ser Gly Met Lys Ala Thr Met Phe Ala Ala Gln Ser Ile Gln Leu Gly
                100                 105                 110

Ile Asn Asp Ile Val Val Ala Gly Gly Met Glu Ser Met Ser Asn Ala
            115                 120                 125

-continued

```
Pro Lys Tyr Ile Ala Glu Ala Arg Lys Gly Ser Arg Phe Gly His Asp
    130                 135                 140

Thr Leu Val Asp Ala Met Leu Lys Asp Gly Leu Trp Asp Val Tyr Asn
145                 150                 155                 160

Asp Cys Ala Met Gly Met Cys Ala Glu Leu Cys Ala Asp Asn His Ala
                165                 170                 175

Leu Thr Arg Glu Asp Gln Asp Ala Phe Ala Ile Gln Ser Asn Glu Arg
            180                 185                 190

Gly Ile Ala Ala Arg Asp Ser Gly Ala Phe Ala Trp Glu Ile Ile Pro
        195                 200                 205

Val Gln Val Pro Val Gly Arg Gly Lys Pro Pro Thr Leu Ile Glu Arg
    210                 215                 220

Asp Glu Ser Leu Asp Lys Phe Asp Pro Val Lys Leu Lys Lys Leu Arg
225                 230                 235                 240

Pro Ser Phe Lys Glu Asn Gly Gly Thr Val Thr Ala Gly Asn Ala Ser
                245                 250                 255

Ser Ile Ser Asp Gly Ala Ala Ala Leu Val Leu Val Ser Gly Gln Lys
            260                 265                 270

Ala Gln Glu Leu Gly Leu Gln Val Leu Ala Arg Ile Lys Gly Tyr Ala
        275                 280                 285

Asp Ala Ala Gln Ala Pro Glu Leu Phe Thr Thr Thr Pro Ala Leu Ala
    290                 295                 300

Ile Pro Lys Ala Ile Ala Asn Ala Gly Leu Glu Ser Ser Arg Val Asp
305                 310                 315                 320

Phe Tyr Glu Ile Asn Glu Ala Phe Ser Ala Val Ala Leu Ala Asn Gln
                325                 330                 335

Lys Leu Leu Gly Ile Pro Ser Glu Lys Ile Asn Val His Gly Gly Ala
            340                 345                 350

Val Ser Leu Gly His Pro Leu Gly Cys Ser Gly Ala Arg Ile Leu Val
        355                 360                 365

Thr Leu Ile Gly Val Leu Arg Ala Lys Ser Gly Lys Ile Gly Val Ala
    370                 375                 380

Gly Val Cys Asn Gly Gly Gly Gly Ala Ser Ala Leu Val Leu Glu Leu
385                 390                 395                 400

Ala
```

<210> SEQ ID NO 19
<211> LENGTH: 2128
<212> TYPE: DNA
<213> ORGANISM: Oryza sativa

<400> SEQUENCE: 19

```
aatgggtttg ccattcagag gagcaaagtt gagcagctcc agtgctcttg cagcatccac     60
ggggttgttg aagttgacgt aggcgtagcc gagcgagcgg cgcgagctga tgtccctgca    120
gacgcgcacc gacatcacct gccccgcctg gctgaagagc tcgtacagct gcgagtccgt    180
gaccgacgcc tccaggtcgc ccacgtacag cgactgcgcc ccgccgcccc cgaggcccac    240
ggcgacgccg accctcccg ccgccgccgc cgcggtgaca gccccggag agcccccgtt     300
caccgccacc gccgccattt gcgccgccat cgcccaccga tccctcgacc tgctcccctc    360
acccttctct ctttttcaat tttttttcgc gaaacaaaaa aaaaaatct gctctaaacc    420
ctagctgatg gattggtata tagctcggca cgggcagatc tcgcggagtt ttggggaaa    480
tttttttct cttttttctt tggtgtgat actagaaatt ttttttttt gggagtagtt    540
```

-continued

```
tttggttgcg ggatacaaga ggccgtaggc ggagagcacg cggcggaggc gaggtttaaa      600
cctcgtgccg aattcggcac gaggtttaaa catcctgccg ttgccacgtt cccgtgtcgt      660
tttgctcctc acccgcgatc tcctctcctc tccgcctaaa cccctccct cctccgcctc       720
gttcactccg ccgccgccgc cgccgccaga tccagcagct tcaggtcggg gctgaacctt      780
ggacttggag cggccatggc ttcggacaac attggctcga gagatgtatg tgttgttggg      840
gttgcacgca ccctatggg tggtttccta ggtgccctgt cttccttgtc agctaccaaa       900
cttggttcca tagcaattga agctgctctg aagagggcaa atgttgatcc agcccttgtg      960
caagaggtct tctttggtaa tgtgttgagt gctaatttgg ggcaagctcc tgcaagacaa     1020
gctgctttag gtgcagggat accaaacaca gttgtttgca gcgcagttaa caaagtttgc     1080
gcatctggca tgaaagcgac aatgtttgca gcacagtcaa ttctattggg catcaatgat     1140
attgttgtag ccggtggcat ggaaagcatg tctaatgctc caaaatacat tgctgaagct     1200
agaaaaggat ctcgttttgg acatgacact cttgttgatg gcatgcttaa agatggcctt     1260
tgggatgtat acggtgattt tgccatggga aattgtgctg agctttgtgc tgacaatcat     1320
gctctgacaa gggaagacca ggatgcctat gctattcaaa gcaatgagcg tggaattgct     1380
gctcggaaca gtggtgcttt tgcatgggag attgttccga ttgaagttcc tgttgggaga     1440
gggaaaccac cggtacttgt tgacaaagat gagggcctgg acaagtttga cccagtgaaa     1500
ctgaagaagc tccgtcctag tttcaaggag aatggtggta ctgttactgc tgggaatgct     1560
tctagtataa gtgacggtgc tgccgcatta gtattggtga gtgggcagaa ggcacaagaa     1620
cttggactgc aagttattgc acgaatcaaa ggatttgcag atgcagctca agctcctgaa     1680
ttatttacca ctagcccggc acttgccata cctaaggctc ttgctaatgc tggcttggag     1740
tcttctcgtg ttgattacta tgaaattaat gaagcctttt cagctgttgc acttgcaaat     1800
caaaagcttc ttggaattcc ttcagaaaaa attaatgtac atggaggagc tgtgtcttta     1860
ggacatcctc ttggatgcag tggtgctcga attttggtca ccctgcttgg tgttcttagg     1920
gagaaaggtg gcaaaatcgg agttgctggt gtttgcaatg gcgaggcgg agcatctgct     1980
ctcgttctcg agcttgcata agaagccttg tgatccatct ccagttctcc aggacgtttg     2040
tgtactctag tttatttgat tttctgcttt agctgtttgg acattctttt atcttaataa     2100
ttgggtaata agtgtgttt gtggtgcc                                         2128
```

<210> SEQ ID NO 20
<211> LENGTH: 401
<212> TYPE: PRT
<213> ORGANISM: Oryza sativa

<400> SEQUENCE: 20

| Met | Ala | Ser | Asp | Asn | Ile | Gly | Ser | Arg | Asp | Val | Cys | Val | Val | Gly | Val |
|---|---|---|---|---|---|---|---|---|---|---|---|---|---|---|---|
| 1 | | | | 5 | | | | | 10 | | | | | 15 | |

| Ala | Arg | Thr | Pro | Met | Gly | Gly | Phe | Leu | Gly | Ala | Leu | Ser | Ser | Leu | Ser |
|---|---|---|---|---|---|---|---|---|---|---|---|---|---|---|---|
| | | | 20 | | | | | 25 | | | | | 30 | | |

| Ala | Thr | Lys | Leu | Gly | Ser | Ile | Ala | Ile | Glu | Ala | Ala | Leu | Lys | Arg | Ala |
|---|---|---|---|---|---|---|---|---|---|---|---|---|---|---|---|
| | | | 35 | | | | | 40 | | | | | 45 | | |

| Asn | Val | Asp | Pro | Ala | Leu | Val | Gln | Glu | Val | Phe | Phe | Gly | Asn | Val | Leu |
|---|---|---|---|---|---|---|---|---|---|---|---|---|---|---|---|
| | | 50 | | | | | 55 | | | | | 60 | | | |

| Ser | Ala | Asn | Leu | Gly | Gln | Ala | Pro | Ala | Arg | Gln | Ala | Ala | Leu | Gly | Ala |
|---|---|---|---|---|---|---|---|---|---|---|---|---|---|---|---|
| 65 | | | | | 70 | | | | | 75 | | | | | 80 |

| Gly | Ile | Pro | Asn | Thr | Val | Val | Cys | Ser | Ala | Val | Asn | Lys | Val | Cys | Ala |
|---|---|---|---|---|---|---|---|---|---|---|---|---|---|---|---|

```
                85                  90                  95
Ser Gly Met Lys Ala Thr Met Phe Ala Ala Gln Ser Ile Leu Leu Gly
            100                 105                 110

Ile Asn Asp Ile Val Val Ala Gly Gly Met Glu Ser Met Ser Asn Ala
            115                 120                 125

Pro Lys Tyr Ile Ala Glu Ala Arg Lys Gly Ser Arg Phe Gly His Asp
            130                 135                 140

Thr Leu Val Asp Gly Met Leu Lys Asp Gly Leu Trp Asp Val Tyr Gly
145                 150                 155                 160

Asp Phe Ala Met Gly Asn Cys Ala Glu Leu Cys Ala Asp Asn His Ala
                165                 170                 175

Leu Thr Arg Glu Asp Gln Asp Ala Tyr Ala Ile Gln Ser Asn Glu Arg
            180                 185                 190

Gly Ile Ala Ala Arg Asn Ser Gly Ala Phe Ala Trp Glu Ile Val Pro
            195                 200                 205

Ile Glu Val Pro Val Gly Arg Gly Lys Pro Pro Val Leu Val Asp Lys
            210                 215                 220

Asp Glu Gly Leu Asp Lys Phe Asp Pro Val Lys Leu Lys Lys Leu Arg
225                 230                 235                 240

Pro Ser Phe Lys Glu Asn Gly Gly Thr Val Thr Ala Gly Asn Ala Ser
                245                 250                 255

Ser Ile Ser Asp Gly Ala Ala Ala Leu Val Leu Val Ser Gly Gln Lys
            260                 265                 270

Ala Gln Glu Leu Gly Leu Gln Val Ile Ala Arg Ile Lys Gly Phe Ala
            275                 280                 285

Asp Ala Ala Gln Ala Pro Glu Leu Phe Thr Thr Ser Pro Ala Leu Ala
290                 295                 300

Ile Pro Lys Ala Leu Ala Asn Ala Gly Leu Glu Ser Ser Arg Val Asp
305                 310                 315                 320

Tyr Tyr Glu Ile Asn Glu Ala Phe Ser Ala Val Ala Leu Ala Asn Gln
                325                 330                 335

Lys Leu Leu Gly Ile Pro Ser Glu Lys Ile Asn Val His Gly Gly Ala
            340                 345                 350

Val Ser Leu Gly His Pro Leu Gly Cys Ser Gly Ala Arg Ile Leu Val
            355                 360                 365

Thr Leu Leu Gly Val Leu Arg Glu Lys Gly Gly Lys Ile Gly Val Ala
            370                 375                 380

Gly Val Cys Asn Gly Gly Gly Gly Ala Ser Ala Leu Val Leu Glu Leu
385                 390                 395                 400

Ala

<210> SEQ ID NO 21
<211> LENGTH: 1593
<212> TYPE: DNA
<213> ORGANISM: Glycine max

<400> SEQUENCE: 21
gcacgagtct ctctcttttt cgcctcattc cattttcatc tatcaatggc tccagtagca      60
gcagcatctt cagattcaat caagccaaga gatgtttgca tcgttggtgt tgcacgtaca     120
ccaatgggtg gatttcttgg tactctgtca tctctatctg ccaccaagct aggctctata     180
gctattgaag ctgctcttaa aagggccaat gttgatccat cccttgtgga agaagtattt     240
tttgggaatg ttcttagtgc taatttgggg caagctcctg caagacaagc tgctcttgga     300
```

-continued

```
gcaggaatat ccaattcagt tatctgcact accgttaaca agtttgtgc atcaggaatg      360
aaagctgcaa tgcttgctgc acagagtatt caattaggca caaatgatgt tgttgtggct    420
ggtggtatgg aaagcatgtc taatgtaccc aagtacctgg ctgaagcaag gaaaggatca    480
cgccttggac atgattcact tgttgatggg atgttgaaag atggtttgtg ggatgtctat    540
aaggatgttg gcatgggagt gtgtgctgag ctatgtgcag ataaccatgc attaacaaga    600
gacgaccagg ataactatgc aattcagagt tttgaacgtg gaattgctgc caagaaagt    660
ggtgcctttt catgggaaat tgctccagtt gaagtctctg gtggaagagg aagaccatca    720
acagttgttg ataaggatga aggcctagga agtttgatg ctgccaagtt acgcaaactt     780
cggccaagtt tcaaggagac tggaggttct gttacagctg caatgcttc cagcataagt     840
gatggtgctg ctgcactagt tttggtgagt ggagagaagg cactgaagct tgggcttcaa    900
gttattgcaa aaatcactgg atatgctgat gctgctcagg aaccagagtt atttacaacg    960
gctccatccc ttgccattcc caaagctatt gccaaggcgg ggttggagac ttcacaaatt   1020
gatttttatg aaattaatga agcctttgcg ttgtggctc tcgcaaatca gaaacttctt    1080
ggacttaact cggaaaaagt aaacgtacat ggtggagctc ttgcactggg tcatcctctt   1140
ggttgcagtg gtgctcgcat tctggtgaca cttttggggg tactgaagca aagaatggg    1200
aagtacggag ttggtggcat ttgcaatgga ggagtggtg catctgccct tgttgttgag    1260
cttcagtaag acctatttca tgttcagtag atgtcctttt aagagccagc gtttgatgca   1320
aagctcaaaa gatcttgcct ccctctttag caagcgaaca tgcaagtttc aaatttatta   1380
caaggacaag accgaaagag agcgaaattt agctacatag ttgttaggtt taagtcgcat   1440
cttgtgaaag tgaaattttc ttggcatcaa agtagaacat gaaacaatat tatccaaatt   1500
ttagttttct ctgaaatgtt attggcgtac tttggtttgg aatgaatcat tataaaacct   1560
cttattccaa gcacaaaaaa aaaaaaaaaa aaa                                1593
```

<210> SEQ ID NO 22
<211> LENGTH: 407
<212> TYPE: PRT
<213> ORGANISM: Glycine max

<400> SEQUENCE: 22

```
Met Ala Pro Val Ala Ala Ser Ser Asp Ser Ile Lys Pro Arg Asp
1               5                   10                  15

Val Cys Ile Val Gly Val Ala Arg Thr Pro Met Gly Gly Phe Leu Gly
            20                  25                  30

Thr Leu Ser Ser Leu Ser Ala Thr Lys Leu Gly Ser Ile Ala Ile Glu
        35                  40                  45

Ala Ala Leu Lys Arg Ala Asn Val Asp Pro Ser Leu Val Glu Glu Val
    50                  55                  60

Phe Phe Gly Asn Val Leu Ser Ala Asn Leu Gly Gln Ala Pro Ala Arg
65                  70                  75                  80

Gln Ala Ala Leu Gly Ala Gly Ile Ser Asn Ser Val Ile Cys Thr Thr
                85                  90                  95

Val Asn Lys Val Cys Ala Ser Gly Met Lys Ala Ala Met Leu Ala Ala
            100                 105                 110

Gln Ser Ile Gln Leu Gly Thr Asn Asp Val Val Ala Gly Gly Met
        115                 120                 125

Glu Ser Met Ser Asn Val Pro Lys Tyr Leu Ala Glu Ala Arg Lys Gly
    130                 135                 140
```

```
Ser Arg Leu Gly His Asp Ser Leu Val Asp Gly Met Leu Lys Asp Gly
145                 150                 155                 160

Leu Trp Asp Val Tyr Lys Asp Val Gly Met Gly Val Cys Ala Glu Leu
                165                 170                 175

Cys Ala Asp Asn His Ala Leu Thr Arg Asp Asp Gln Asp Asn Tyr Ala
            180                 185                 190

Ile Gln Ser Phe Glu Arg Gly Ile Ala Ala Gln Glu Ser Gly Ala Phe
        195                 200                 205

Ser Trp Glu Ile Ala Pro Val Glu Val Ser Gly Gly Arg Gly Arg Pro
210                 215                 220

Ser Thr Val Val Asp Lys Asp Glu Gly Leu Gly Lys Phe Asp Ala Ala
225                 230                 235                 240

Lys Leu Arg Lys Leu Arg Pro Ser Phe Lys Glu Thr Gly Gly Ser Val
                245                 250                 255

Thr Ala Gly Asn Ala Ser Ser Ile Ser Asp Gly Ala Ala Ala Leu Val
            260                 265                 270

Leu Val Ser Gly Glu Lys Ala Leu Lys Leu Gly Leu Gln Val Ile Ala
        275                 280                 285

Lys Ile Thr Gly Tyr Ala Asp Ala Ala Gln Glu Pro Glu Leu Phe Thr
290                 295                 300

Thr Ala Pro Ser Leu Ala Ile Pro Lys Ala Ile Ala Lys Ala Gly Leu
305                 310                 315                 320

Glu Thr Ser Gln Ile Asp Phe Tyr Glu Ile Asn Glu Ala Phe Ala Val
                325                 330                 335

Val Ala Leu Ala Asn Gln Lys Leu Leu Gly Leu Asn Ser Glu Lys Val
            340                 345                 350

Asn Val His Gly Gly Ala Val Ala Leu Gly His Pro Leu Gly Cys Ser
        355                 360                 365

Gly Ala Arg Ile Leu Val Thr Leu Leu Gly Val Leu Lys Gln Lys Asn
370                 375                 380

Gly Lys Tyr Gly Val Gly Gly Ile Cys Asn Gly Gly Gly Gly Ala Ser
385                 390                 395                 400

Ala Leu Val Val Glu Leu Gln
                405

<210> SEQ ID NO 23
<211> LENGTH: 876
<212> TYPE: DNA
<213> ORGANISM: Triticum aestivum

<400> SEQUENCE: 23
gcacgagatt caaagtaatg agcgtggaat tgctgctcgt gacagtggtg cttttgcatg      60
ggagattgtt ccgattgaag ttcctgttgg tagagggaaa cctgcagtac ttgttgacaa     120
agatgagagc ctagacaagt tgacgcagc caagctgaag aagttacgac cagcattcaa     180
ggagaatgct ggtactgtta ctgctggaaa tgcttctagt ataagtgatg gtgctgcagc     240
attagtattg gtgagtggga agaaggctca agaacttgga ttgcaagtcc ttgcaaggat     300
taagggattt gccgatgcag cccaagctcc tgaactattt accactaccc cagcacttgc     360
cataccgaag gctctcacaa atgctggcct agagtcctct cgtattgatt tttatgaaat     420
caatgaagcc ttttcggctg ttgcacttgc aaatcaaaag cttctcggaa ttccttcaga     480
aaagataaat gtacatggag gagctgtatc tttaggacac ccacttgggt gcagtggtgc     540
tcgcattttg gtcacccttc tcggtgttct tagggagaag agtggcaaga tcggagttgc     600
```

```
tggtgtctgc aacggcggtg gcggtgcatc tgcgctcgtt atggagctgg cgtaaggagc    660
tctgacacca agatggagc ctgcatgtaa aattctatgt actgtatttc atagtgctgt    720
gtcagattaa gtaattgatt aacttagaac ttgtgtgccg gtttctgatc ttactctaga    780
ttgtttcaat tttcttttct gttgtagctg ttttaagcat tcttggttta ataacaataa    840
taataattgt tgcaaaaaaa aaaaaaaaaa aaaaaa                               876
```

<210> SEQ ID NO 24
<211> LENGTH: 196
<212> TYPE: PRT
<213> ORGANISM: Triticum aestivum

<400> SEQUENCE: 24

```
Phe Ala Trp Glu Ile Val Pro Ile Glu Val Pro Val Gly Arg Gly Lys
 1               5                  10                  15

Pro Ala Val Leu Val Asp Lys Asp Glu Ser Leu Asp Lys Phe Asp Ala
            20                  25                  30

Ala Lys Leu Lys Lys Leu Arg Pro Ala Phe Lys Glu Asn Ala Gly Thr
        35                  40                  45

Val Thr Ala Gly Asn Ala Ser Ser Ile Ser Asp Gly Ala Ala Ala Leu
    50                  55                  60

Val Leu Val Ser Gly Lys Lys Ala Gln Glu Leu Gly Leu Gln Val Leu
65                  70                  75                  80

Ala Arg Ile Lys Gly Phe Ala Asp Ala Ala Gln Ala Pro Glu Leu Phe
                85                  90                  95

Thr Thr Thr Pro Ala Leu Ala Ile Pro Lys Ala Leu Thr Asn Ala Gly
            100                 105                 110

Leu Glu Ser Ser Arg Ile Asp Phe Tyr Glu Ile Asn Glu Ala Phe Ser
        115                 120                 125

Ala Val Ala Leu Ala Asn Gln Lys Leu Leu Gly Ile Pro Ser Glu Lys
    130                 135                 140

Ile Asn Val His Gly Gly Ala Val Ser Leu Gly His Pro Leu Gly Cys
145                 150                 155                 160

Ser Gly Ala Arg Ile Leu Val Thr Leu Leu Gly Val Leu Arg Glu Lys
                165                 170                 175

Ser Gly Lys Ile Gly Val Ala Gly Val Cys Asn Gly Gly Gly Gly Ala
            180                 185                 190

Ser Ala Leu Val
        195
```

<210> SEQ ID NO 25
<211> LENGTH: 1796
<212> TYPE: DNA
<213> ORGANISM: Zea mays

<400> SEQUENCE: 25

```
gcacgagggt aacccagagt ccgacgcacg cctagggctc ctggacacag cagagcccac    60
gccttgactc gctccgttcg agtggagcgc acaggcaccg gccggcgacc agagagggag   120
cggatcgagg gggctcggct tgagtggagg agatggaccg caaggatgtc gggatcctcg   180
ccatggacat ctacttcccg ccctcctgcg tgcagcagga agcacttgag gcccatgatg   240
gggcgagcaa agggaagtac accattgggc ttggcaagat tgcatggcc ttttgcagcg    300 aggtggagga tgtcatctca atgagtttga cggttgtcaa ttctctgctg aaaaaataca   360
agattgatcc caagctaatt ggtcgcttgg aggtgggaag tgaaacagtt atagacaaaa   420
```

-continued

```
gcaaatccat caaaacttgg ctgatgcaga tttttgagga aagtgataat actgacattg    480
aaggtgttga ctccagcaat gcatgttatg gtgggacagc agccctactg aattgtgtga    540
attgggtcga agtaactcc tgggatggcc gttatggtct tgtcgtttgc acggacagcg     600
cggtttatgc ggaaggacca gctcgtccaa caggaggtgc tgctgctata gcaatgctca    660
ttggtcctaa tgctccgatt cctttgaga gcaaatatag agcttctcat atggctcatg     720
tttatgattt ctacaaacct gatcttgcaa gtgaatatcc ggttgttgat ggtaaattat    780
cccaaacatg ctacctgatg gctcttgact catgctacag acagttctgc aacaagtatg    840
agaagattgc gggtaaacaa ttctcaattt cagatgcaga atattttgtg ttccattctc    900
catacaacaa gctcgtgcag aagagttttg ctcgacttta ctacaatgac ttcatgcgca    960
actgcagcta tgttgatgat gatgttaaag agaagctcca gtccttttca aatttgactg   1020
gtgaagagag ctaccagagt cgcgacttgg aaaaggcctc acaacaggtc gcaaagcacc   1080
tgtatggcat caaagttcag ccaacgactc tgcttccgaa acagatcggc aacatgtata   1140
cggcatccct ttatgctgca ttggcatctg tgctatataa caagcatgat agtctgaatg   1200
gacaaagaat tgtgatgttc tcttacggca gcggcttgac atccactatg ttttcgttga   1260
ggctaaacaa tggccagcat cccttcagtc tatcaaacat aggttcagtt cttggtgtca   1320
ccgagaagct tcagtcaaga catgagacct tgcctgagaa attcgttgag acgctgaagc   1380
tgatggaaca ccgatacggc gcaaaagact tcgagacgag cagcgacacg agtctcctgc   1440
agccgggcac attctacctc accaaggtgg actccatgta ccggaggttc tattcccaga   1500
agccggccga ggaaacaggc ggcggtaaaa ccaagtgctg caacggcttc gcaaatggcc   1560
actagtggga gtccgcgtgc cgtttgaatt gctacgtcgc ccttctgtac tgttgatcat   1620
cattctctgt gttttgatca tgcttgtggt tagcgttttc accctagggt gtttctgaaa   1680
taatatatta ctagatatat ccccatctgt tacatcgggg tcacgaattt tgccatttag   1740
gccttctcta tttttctta gttatttatt gactctctaa aaaaaaaaa aaaaaa        1796
```

<210> SEQ ID NO 26
<211> LENGTH: 470
<212> TYPE: PRT
<213> ORGANISM: Zea mays

<400> SEQUENCE: 26

```
Met Asp Arg Lys Asp Val Gly Ile Leu Ala Met Asp Ile Tyr Phe Pro
1               5                   10                  15

Pro Ser Cys Val Gln Gln Glu Ala Leu Glu Ala His Asp Gly Ala Ser
                20                  25                  30

Lys Gly Lys Tyr Thr Ile Gly Leu Gly Gln Asp Cys Met Ala Phe Cys
            35                  40                  45

Ser Glu Val Glu Asp Val Ile Ser Met Ser Leu Thr Val Val Asn Ser
        50                  55                  60

Leu Leu Lys Lys Tyr Lys Ile Asp Pro Lys Leu Ile Gly Arg Leu Glu
65                  70                  75                  80

Val Gly Ser Glu Thr Val Ile Asp Lys Ser Lys Ser Ile Lys Thr Trp
                85                  90                  95

Leu Met Gln Ile Phe Glu Glu Ser Asp Asn Thr Asp Ile Glu Gly Val
                100                 105                 110

Asp Ser Ser Asn Ala Cys Tyr Gly Gly Thr Ala Ala Leu Leu Asn Cys
            115                 120                 125

Val Asn Trp Val Glu Ser Asn Ser Trp Asp Gly Arg Tyr Gly Leu Val
```

```
                130               135               140
Val Cys Thr Asp Ser Ala Val Tyr Ala Glu Gly Pro Ala Arg Pro Thr
145                 150                 155                 160

Gly Gly Ala Ala Ala Ile Ala Met Leu Ile Gly Pro Asn Ala Pro Ile
                165                 170                 175

Ser Phe Glu Ser Lys Tyr Arg Ala Ser His Met Ala His Val Tyr Asp
                180                 185                 190

Phe Tyr Lys Pro Asp Leu Ala Ser Glu Tyr Pro Val Asp Gly Lys
                195                 200                 205

Leu Ser Gln Thr Cys Tyr Leu Met Ala Leu Asp Ser Cys Tyr Arg Gln
210                 215                 220

Phe Cys Asn Lys Tyr Glu Lys Ile Ala Gly Lys Gln Phe Ser Ile Ser
225                 230                 235                 240

Asp Ala Glu Tyr Phe Val Phe His Ser Pro Tyr Asn Lys Leu Val Gln
                245                 250                 255

Lys Ser Phe Ala Arg Leu Tyr Tyr Asn Asp Phe Met Arg Asn Cys Ser
                260                 265                 270

Tyr Val Asp Asp Val Lys Glu Lys Leu Gln Ser Phe Ser Asn Leu
275                 280                 285

Thr Gly Glu Glu Ser Tyr Gln Ser Arg Asp Leu Glu Lys Ala Ser Gln
290                 295                 300

Gln Val Ala Lys His Leu Tyr Gly Ile Lys Val Gln Pro Thr Thr Leu
305                 310                 315                 320

Leu Pro Lys Gln Ile Gly Asn Met Tyr Thr Ala Ser Leu Tyr Ala Ala
                325                 330                 335

Leu Ala Ser Val Leu Tyr Asn Lys His Asp Ser Leu Asn Gly Gln Arg
                340                 345                 350

Ile Val Met Phe Ser Tyr Gly Ser Gly Leu Thr Ser Thr Met Phe Ser
                355                 360                 365

Leu Arg Leu Asn Asn Gly Gln His Pro Phe Ser Leu Ser Asn Ile Gly
370                 375                 380

Ser Val Leu Gly Val Thr Glu Lys Leu Gln Ser Arg His Glu Thr Leu
385                 390                 395                 400

Pro Glu Lys Phe Val Glu Thr Leu Lys Leu Met Glu His Arg Tyr Gly
                405                 410                 415

Ala Lys Asp Phe Glu Thr Ser Ser Asp Thr Ser Leu Leu Gln Pro Gly
                420                 425                 430

Thr Phe Tyr Leu Thr Lys Val Asp Ser Met Tyr Arg Arg Phe Tyr Ser
                435                 440                 445

Gln Lys Pro Ala Glu Glu Thr Gly Gly Gly Lys Thr Lys Cys Cys Asn
450                 455                 460

Gly Phe Ala Asn Gly His
465                 470

<210> SEQ ID NO 27
<211> LENGTH: 1766
<212> TYPE: DNA
<213> ORGANISM: Oryza sativa

<400> SEQUENCE: 27
gcacgagctc tgctctagcg tgggcggaga acacgaggcg tggccgcgtc gtcgtcggag      60
gagggagcag agatggacgg ccgcaaggat gtcgggatcc tcgccatgga tatctacttc     120
ccgcccacct gcgtcctcca ggaatcgctc gaggctcatg acggcgccag caaagggaag     180
```

-continued

```
tacaccattg gtctcggcca agattgcatg gccttctgca gtgaggtgga ggatgtcatc      240
tcgatgagca tgacagttgt cacatccctg ctgaaaaaat acaaggtcga tccaaagctg      300
attggtcgat tggaggttgg cagtgagaca gtcatagaca agagcaaatc catcaagact      360
tggctgatgc agattttcga ggaatgcggt aatactgaca ttgaaggagt tgattccagt      420
aacgcgtgtt atggtgggac agcagcgctg ttgaattgtg tgaactgggt tgagagtaac      480
tcctgggatg gacgctatgg ccttgttgtt tgcacggaca gcgcggttta tgcggaaggc      540
ccagctcgtc cgacaggtgg tgctgctgct attgcaatgc tcattggtcc taatgctcct      600
attgcattcg agagcaaata caaagcttct cacatggctc acgtctatga tttctataag      660
cctgatcttg caagtgaata tccggtcgtt gatggaaaac tatcccaaac atgctacttg      720
atggcgctag actcatgcta cagacagttt tgtaagaagt atgaaaagct ggcggggaaa      780
caattctcaa tttctgatgc agattacttt gttttccatt ctccatacaa caagcttgtg      840
cagaagagtt ttgctcggct ttactataat gatttcacgc gcgactgcag ctctgttgac      900
aatgatgcta agagaagct ccagcctttc tcaaatttga ctggcgagga gagctaccaa      960
agtcgtgact tggaaaaggc ttcacaacaa gtagcaaagc ccttgtatga catcaaagtt     1020
caaccatcaa ctttgcttcc aaaacaaatt ggtaacatgt acacagcatc tctttatgct     1080
gcgttggcgt ctgtactcta taacaagcat gctagtctgg atgaccaacg aattgttatg     1140
ttctcgtacg gcagtggctt gacatccact atgttttcgt gaaacttaa caatggccag      1200 gaccccttca gtttatcaaa cattgcttca gtgcttaatg ccacggagaa gcttgagtca     1260
agacatatga ccttgcccga gaaatttgtg gagacgctga agctgatgga gcaccgatac     1320
ggcgcaaaag atttcgagac gtgcaaagac acgagcttgt tgcctcctgg gacgttctac     1380
ctcaccaggg ttgactccat gtaccgaaga ttctatgaga ggaaggccga cgaggagatc     1440
gctgcagcca agccaagta cagtaatgga catgccacca atggctatgc caatggccac     1500
tagtggcacg catggcatga tggctgctgc tgatattgat ttctggtttg ataagttcat     1560
gattaggtgt ttccagccta gtgtagtagt ttctcaaata agtgttctcc acacctgtta     1620
tccatatctc ctctaatttt tttgtattga atcagacaga ctagtgagac atttctgtag     1680
tatcaatcat tcttgtttct tcttaaaaaa aaaaaaaaaa aaaaaaaaaa aaaaaaaaaa     1740
aaaaaaaaaa aaaaaaaaaa aaaaaa                                         1766
```

<210> SEQ ID NO 28
<211> LENGTH: 476
<212> TYPE: PRT
<213> ORGANISM: Oryza sativa

<400> SEQUENCE: 28

```
Met Asp Gly Arg Lys Asp Val Gly Ile Leu Ala Met Asp Ile Tyr Phe
1               5                   10                  15

Pro Pro Thr Cys Val Leu Gln Glu Ser Leu Glu Ala His Asp Gly Ala
            20                  25                  30

Ser Lys Gly Lys Tyr Thr Ile Gly Leu Gly Gln Asp Cys Met Ala Phe
        35                  40                  45

Cys Ser Glu Val Glu Asp Val Ile Ser Met Ser Met Thr Val Val Thr
    50                  55                  60

Ser Leu Leu Lys Lys Tyr Lys Val Asp Pro Lys Leu Ile Gly Arg Leu
65                  70                  75                  80

Glu Val Gly Ser Glu Thr Val Ile Asp Lys Ser Lys Ser Ile Lys Thr
                85                  90                  95
```

-continued

Trp Leu Met Gln Ile Phe Glu Glu Cys Gly Asn Thr Asp Ile Glu Gly
            100                 105                 110

Val Asp Ser Ser Asn Ala Cys Tyr Gly Gly Thr Ala Ala Leu Leu Asn
        115                 120                 125

Cys Val Asn Trp Val Glu Ser Asn Ser Trp Asp Gly Arg Tyr Gly Leu
    130                 135                 140

Val Val Cys Thr Asp Ser Ala Val Tyr Ala Glu Gly Pro Ala Arg Pro
145                 150                 155                 160

Thr Gly Gly Ala Ala Ile Ala Met Leu Ile Gly Pro Asn Ala Pro
                165                 170                 175

Ile Ala Phe Glu Ser Lys Tyr Lys Ala Ser His Met Ala His Val Tyr
            180                 185                 190

Asp Phe Tyr Lys Pro Asp Leu Ala Ser Glu Tyr Pro Val Val Asp Gly
        195                 200                 205

Lys Leu Ser Gln Thr Cys Tyr Leu Met Ala Leu Asp Ser Cys Tyr Arg
    210                 215                 220

Gln Phe Cys Lys Lys Tyr Glu Lys Leu Ala Gly Lys Gln Phe Ser Ile
225                 230                 235                 240

Ser Asp Ala Asp Tyr Phe Val Phe His Ser Pro Tyr Asn Lys Leu Val
                245                 250                 255

Gln Lys Ser Phe Ala Arg Leu Tyr Tyr Asn Asp Phe Thr Arg Asp Cys
            260                 265                 270

Ser Ser Val Asp Asn Asp Ala Lys Glu Lys Leu Gln Pro Phe Ser Asn
        275                 280                 285

Leu Thr Gly Glu Glu Ser Tyr Gln Ser Arg Asp Leu Glu Lys Ala Ser
    290                 295                 300

Gln Gln Val Ala Lys Pro Leu Tyr Asp Ile Lys Val Gln Pro Ser Thr
305                 310                 315                 320

Leu Leu Pro Lys Gln Ile Gly Asn Met Tyr Thr Ala Ser Leu Tyr Ala
                325                 330                 335

Ala Leu Ala Ser Val Leu Tyr Asn Lys His Ala Ser Leu Asp Asp Gln
            340                 345                 350

Arg Ile Val Met Phe Ser Tyr Gly Ser Gly Leu Thr Ser Thr Met Phe
        355                 360                 365

Ser Leu Lys Leu Asn Asn Gly Gln Asp Pro Phe Ser Leu Ser Asn Ile
    370                 375                 380

Ala Ser Val Leu Asn Ala Thr Glu Lys Leu Glu Ser Arg His Met Thr
385                 390                 395                 400

Leu Pro Glu Lys Phe Val Glu Thr Leu Lys Leu Met Glu His Arg Tyr
                405                 410                 415

Gly Ala Lys Asp Phe Glu Thr Cys Lys Asp Thr Ser Leu Leu Pro Pro
            420                 425                 430

Gly Thr Phe Tyr Leu Thr Arg Val Asp Ser Met Tyr Arg Arg Phe Tyr
        435                 440                 445

Glu Arg Lys Ala Asp Glu Glu Ile Ala Ala Lys Ala Lys Tyr Ser
    450                 455                 460

Asn Gly His Ala Thr Asn Gly Tyr Ala Asn Gly His
465                 470                 475

<210> SEQ ID NO 29
<211> LENGTH: 1741
<212> TYPE: DNA
<213> ORGANISM: Glycine max -continued

```
<400> SEQUENCE: 29
tcaaaatcac ataaggtcct cgctgctgct aagtgcctcc ttcttcctcc tatatatata      60
tatatataca tatatgcacg taaagcctct tcgcacaact taaccctctc tctctgagat     120
ggcaaagaat gtggggattc tcgctatcga catctacttc cctcccacct gtattcagca     180
ggaattgctg gaggctcatg atggtgccag taaagggaaa tatactattg gacttggtca     240
agattgcatg gcgttttgta cagaagtaga agatgtcatc tcgatgagtt tgacagtagt     300
ttcttccctt cttgaaaagt atgcgattga tcctaaacaa attggtcgtc tggaagtagg     360
cagtgagact gtgattgaca aaagcaaatc catcaaaact ttcatcatgc aaatctttga     420
gaaatatgga ataccgata ttgagggcgt tgattcaact aatgcatgct atggaggaac     480
tgctgctttg ttcaattgtg tcaattgggt ggagagcagc tcatgggatg acgctatgg     540
acttgttgtc tgcactgaca gtgctgtcta tgctgaagga cctgctcggc ctactggtgg     600
agccgctgct gttgccatgc taattggtcc tgatgctccc atttcttttg aaagcaaatt     660
gaggggaagt catatggctc atgcctatga ttttttacaag cctaatcttg ccagtgaata     720
tccagtggtt gatgggaagc tttctcaaac ttgttacctt atggcccttg attcttgcta     780
taatcactta agtcacaaat atgagaaaca gagggaaaa caatttttcta tttctgatgc     840
agaatacttt gtatttcact ctccatacaa caagcttgta caaaaaagtt ttgctcgttt     900
ggtgttcaat gacttcttga aaaatgccag ttttgtggat gaggctgcca agaaaaagct     960
ggaaccttt gcaacattat ctggtgatga gagctatcaa agccgggatc tagaaaaggc    1020
atcccagcaa gttgcaaagc tcaatacga tgcaaaggtg cagccaacca ccttgatacc    1080
gaaacaagtt ggcaacatgt acaccgcatc tctttatgca gcctttattt cacttattca    1140
caacaagcat agcacattgg atggtaagag ggtaatattg ttctcgtatg gaagtggctt    1200
aacttccaca atgttctctt tgctattacg tgaaggtcaa catccattta gcctgtcaaa    1260
cattgataaa atgatggatg ttgctgggaa attgaagtca agacatgagt ttccaccaga    1320
gaaatttgtt gaaaccatga agctaatgga acataggtat ggtggcaagg agtttgtaac    1380
aagcaaggac accagccttt tatctccagg cacattctat ctcactgaag ttgactccat    1440
gtataggaga ttctatgcaa agaaaactag tgaaaatggt ttggtcacca atggtcactg    1500
acgtttact tagagaacgt gtaatacctg gaaaccagga attcaactgt gcttagcatt    1560
tagaaggctg ttctcgttg gattagtttc ttcttaaggg aagacaaacg aacaattatg    1620
aaatctgtag gagccaggtg ttgttagttc aaaaattttc cgaaactctt caagtttaaa    1680
tgattccacc aaaaattgtt tctaaaaaaa aaaaaaaaa aaaaaaaaa actcgagact    1740
a                                                                   1741
```

<210> SEQ ID NO 30
<211> LENGTH: 460
<212> TYPE: PRT
<213> ORGANISM: Glycine max

<400> SEQUENCE: 30

```
Met Ala Lys Asn Val Gly Ile Leu Ala Ile Asp Ile Tyr Phe Pro Pro
1               5                   10                  15

Thr Cys Ile Gln Gln Glu Leu Leu Glu Ala His Asp Gly Ala Ser Lys
            20                  25                  30

Gly Lys Tyr Thr Ile Gly Leu Gly Gln Asp Cys Met Ala Phe Cys Thr
        35                  40                  45
```

```
Glu Val Glu Asp Val Ile Ser Met Ser Leu Thr Val Ser Ser Leu
 50                  55                  60

Leu Glu Lys Tyr Ala Ile Asp Pro Lys Gln Ile Gly Arg Leu Glu Val
 65                  70                  75                  80

Gly Ser Glu Thr Val Ile Asp Lys Ser Lys Ser Ile Lys Thr Phe Ile
                     85                  90                  95

Met Gln Ile Phe Glu Lys Tyr Gly Asn Thr Asp Ile Glu Gly Val Asp
                100                 105                 110

Ser Thr Asn Ala Cys Tyr Gly Thr Ala Ala Leu Phe Asn Cys Val
                115                 120                 125

Asn Trp Val Glu Ser Ser Trp Asp Gly Arg Tyr Gly Leu Val Val
            130                 135                 140

Cys Thr Asp Ser Ala Val Tyr Ala Glu Gly Pro Ala Arg Pro Thr Gly
145                 150                 155                 160

Gly Ala Ala Ala Val Ala Met Leu Ile Gly Pro Asp Ala Pro Ile Ser
                165                 170                 175

Phe Glu Ser Lys Leu Arg Gly Ser His Met Ala His Ala Tyr Asp Phe
                180                 185                 190

Tyr Lys Pro Asn Leu Ala Ser Glu Tyr Pro Val Val Asp Gly Lys Leu
                195                 200                 205

Ser Gln Thr Cys Tyr Leu Met Ala Leu Asp Ser Cys Tyr Asn His Leu
            210                 215                 220

Ser His Lys Tyr Glu Lys Gln Glu Gly Lys Gln Phe Ser Ile Ser Asp
225                 230                 235                 240

Ala Glu Tyr Phe Val Phe His Ser Pro Tyr Asn Lys Leu Val Gln Lys
                245                 250                 255

Ser Phe Ala Arg Leu Val Phe Asn Asp Phe Leu Lys Asn Ala Ser Phe
            260                 265                 270

Val Asp Glu Ala Ala Lys Glu Lys Leu Glu Pro Phe Ala Thr Leu Ser
            275                 280                 285

Gly Asp Glu Ser Tyr Gln Ser Arg Asp Leu Glu Lys Ala Ser Gln Gln
            290                 295                 300

Val Ala Lys Pro Gln Tyr Asp Ala Lys Val Gln Pro Thr Thr Leu Ile
305                 310                 315                 320

Pro Lys Gln Val Gly Asn Met Tyr Thr Ala Ser Leu Tyr Ala Ala Phe
                325                 330                 335

Ile Ser Leu Ile His Asn Lys His Ser Thr Leu Asp Gly Lys Arg Val
                340                 345                 350

Ile Leu Phe Ser Tyr Gly Ser Gly Leu Thr Ser Thr Met Phe Ser Leu
            355                 360                 365

Leu Leu Arg Glu Gly Gln His Pro Phe Ser Leu Ser Asn Ile Asp Lys
            370                 375                 380

Met Met Asp Val Ala Gly Lys Leu Lys Ser Arg His Glu Phe Pro Pro
385                 390                 395                 400

Glu Lys Phe Val Glu Thr Met Lys Leu Met Glu His Arg Tyr Gly Gly
                405                 410                 415

Lys Glu Phe Val Thr Ser Lys Asp Thr Ser Leu Leu Ser Pro Gly Thr
                420                 425                 430

Phe Tyr Leu Thr Glu Val Asp Ser Met Tyr Arg Arg Phe Tyr Ala Lys
            435                 440                 445

Lys Thr Ser Glu Asn Gly Leu Val Thr Asn Gly His
450                 455                 460
```

```
<210> SEQ ID NO 31
<211> LENGTH: 639
<212> TYPE: DNA
<213> ORGANISM: Triticum aestivum
<220> FEATURE:
<221> NAME/KEY: unsure
<222> LOCATION: (403)
<223> OTHER INFORMATION: n = A, C, G, or T
<220> FEATURE:
<221> NAME/KEY: unsure
<222> LOCATION: (503)
<223> OTHER INFORMATION: n = A, C, G, or T
<220> FEATURE:
<221> NAME/KEY: unsure
<222> LOCATION: (510)
<223> OTHER INFORMATION: n = A, C, G, or T
<220> FEATURE:
<221> NAME/KEY: unsure
<222> LOCATION: (524)
<223> OTHER INFORMATION: n = A, C, G, or T
<220> FEATURE:
<221> NAME/KEY: unsure
<222> LOCATION: (593)
<223> OTHER INFORMATION: n = A, C, G, or T
<220> FEATURE:
<221> NAME/KEY: unsure
<222> LOCATION: (609)
<223> OTHER INFORMATION: n = A, C, G, or T
<220> FEATURE:
<221> NAME/KEY: unsure
<222> LOCATION: (611)
<223> OTHER INFORMATION: n = A, C, G, or T
<220> FEATURE:
<221> NAME/KEY: unsure
<222> LOCATION: (617)
<223> OTHER INFORMATION: n = A, C, G, or T
<220> FEATURE:
<221> NAME/KEY: unsure
<222> LOCATION: (632)
<223> OTHER INFORMATION: n = A, C, G, or T
<220> FEATURE:
<221> NAME/KEY: unsure
<222> LOCATION: (637)
<223> OTHER INFORMATION: n = A, C, G, or T

<400> SEQUENCE: 31
gaactctctc acgtcacaca cgcctcctcc tgcgagccag ccactgggag agcccgcgga      60
agcacagagc gggaggaggg atcgcgagat ggagtgcaag gatgtcggga tcctcgccat     120
ggacatgtat ttccctccca cctgcgtcca gcaggaagcg ctggaggttc atgacggagc     180
cagcaagggg aagtacacaa ttggtcttgg gcaagattgt atggccttct gcagcgaggt     240
agaagatgtc atctcgatga gcttgacagt tgtcaaatcc ctgctggaaa agtaccacat     300
agatccgaag ctaattggcc gcctggaggt tggtagcgaa acagtgatag acaaaagtaa     360
atccatcaaa acgtggctga tgcaaaattt tgaggaaagt ggnaatacga cattgaagga     420
gttgaccaat taccatttat gtgggacaac tgcctgttga tgtgtgatgg gtccaaatca     480
tctggatggc ctacgctgtt ggnctcacan ataccggtta ccanaggaca accggctacg     540
gaagactctc atgcatgcta tggcaaatca ctaatcttga atataaaact ccnaatggcc     600
aagttcatna naccgtntga ataaaccgtg tntgaanac                            639

<210> SEQ ID NO 32
<211> LENGTH: 115
<212> TYPE: PRT
<213> ORGANISM: Triticum aestivum

<400> SEQUENCE: 32

Lys Asp Val Gly Ile Leu Ala Met Asp Met Tyr Phe Pro Pro Thr Cys
  1               5                  10                  15
```

-continued

Val Gln Gln Glu Ala Leu Glu Val His Asp Gly Ala Ser Lys Gly Lys
    20                  25                  30

Tyr Thr Ile Gly Leu Gly Gln Asp Cys Met Ala Phe Cys Ser Glu Val
        35                  40                  45

Glu Asp Val Ile Ser Met Ser Leu Thr Val Val Lys Ser Leu Leu Glu
    50                  55                  60

Lys Tyr His Ile Asp Pro Lys Leu Ile Gly Arg Leu Glu Val Gly Ser
65                  70                  75                  80

Glu Thr Val Ile Asp Lys Ser Lys Ser Ile Lys Thr Trp Leu Met Gln
                85                  90                  95

Asn Phe Glu Glu Ser Gly Asn Thr Thr Leu Lys Glu Leu Thr Asn Tyr
            100                 105                 110

His Leu Cys
        115

<210> SEQ ID NO 33
<211> LENGTH: 406
<212> TYPE: PRT
<213> ORGANISM: Raphanus sativus

<400> SEQUENCE: 33

Met Ala His Ser Ala Asp Ser Ser Asp Asn Pro Arg Asp Val Cys Ile
1               5                   10                  15

Val Gly Val Ala Arg Thr Pro Met Gly Gly Phe Leu Gly Ser Leu Ser
            20                  25                  30

Ser Leu Pro Ala Thr Lys Leu Gly Ser Leu Ala Ile Thr Ala Ala Leu
        35                  40                  45

Lys Arg Glu Met Leu Thr Arg Leu Trp Ser Lys Glu Val Val Phe Gly
    50                  55                  60

Asn Val Leu Ser Ala Asn Leu Gly Gln Ala Pro Ala Arg Gln Ala Ala
65                  70                  75                  80

Leu Gly Ala Gly Ile Ser Asn Ser Val Ile Cys Thr Thr Val Asn Lys
                85                  90                  95

Val Cys Ala Ser Gly Met Lys Ala Val Met Ile Ala Ala Gln Ser Ile
            100                 105                 110

Gln Leu Gly Ile Asn Asp Val Val Val Ala Gly Gly Met Glu Ser Met
        115                 120                 125

Ser Asn Thr Pro Lys Tyr Leu Ala Glu Ala Arg Lys Gly Ser Arg Phe
    130                 135                 140

Gly His Asp Ser Leu Val Asp Gly Met Leu Lys Asp Gly Leu Trp Asp
145                 150                 155                 160

Val Tyr Asn Asp Cys Gly Met Gly Ser Cys Ala Glu Leu Cys Ala Glu
                165                 170                 175

Lys Phe Glu Ile Thr Arg Glu Gln Gln Asp Asp Tyr Ala Val Gln Ser
            180                 185                 190

Phe Glu Arg Gly Ile Ala Ala Gln Glu Ser Gly Ala Phe Thr Trp Glu
        195                 200                 205

Ile Val Pro Val Glu Val Ser Gly Gly Arg Gly Arg Pro Ser Thr Ile
    210                 215                 220

Val Asp Lys Asp Glu Gly Leu Gly Lys Phe Asp Ala Ala Lys Leu Arg
225                 230                 235                 240

Lys Leu Arg Pro Ser Phe Lys Glu Asn Gly Gly Thr Val Thr Ala Gly
                245                 250                 255

Asn Ala Ser Ser Ile Ser Asp Gly Ala Ala Ala Ile Val Leu Val Ser

```
                    260                 265                 270
Gly Glu Lys Ala Leu Gln Leu Gly Leu Gln Val Leu Ala Lys Val Lys
            275                 280                 285

Gly Tyr Gly Asp Ala Ala Gln Glu Pro Glu Phe Phe Thr Thr Ala Pro
            290                 295                 300

Ala Leu Ala Ile Pro Lys Ala Ile Ala Pro Asn Ser Pro Tyr Ser Glu
305                 310                 315                 320

Ser Tyr Gln Val Asp Tyr Tyr Glu Ile Asn Glu Ala Phe Ala Val Val
                325                 330                 335

Ala Leu Ala Asn Gln Lys Leu Leu Gly Ile Ser Pro Glu Lys Val Asn
            340                 345                 350

Val Asn Gly Gly Ala Val Ser Leu Gly His Pro Leu Gly Cys Ser Gly
            355                 360                 365

Ala Arg Ile Leu Ile Thr Leu Leu Gly Ile Leu Lys Lys Arg Asn Gly
            370                 375                 380

Lys Tyr Gly Val Gly Gly Val Cys Asn Gly Gly Gly Ala Ser Ala
385                 390                 395                 400

Leu Val Leu Glu Val Val
                405

<210> SEQ ID NO 34
<211> LENGTH: 214
<212> TYPE: PRT
<213> ORGANISM: Zea mays

<400> SEQUENCE: 34

Ile Arg His Glu Phe Ala Trp Glu Ile Val Pro Ile Glu Val Pro Val
1               5                   10                  15

Gly Arg Gly Lys Pro Pro Val Leu Ile Glu Lys Asp Glu Ser Leu Asp
                20                  25                  30

Asn Phe Asp Pro Ala Lys Leu Lys Lys Leu Arg Pro Ser Phe Lys Glu
            35                  40                  45

Asn Gly Gly Thr Val Thr Ala Gly Asn Ala Ser Ser Ile Ser Asp Gly
        50                  55                  60

Ala Ala Ala Leu Val Leu Val Ser Gly Gln Lys Ala Gln Glu Leu Gly
65                  70                  75                  80

Leu Gln Val Leu Ala Arg Ile Arg Gly Tyr Ala Asp Ala Ala Gln Ala
                85                  90                  95

Pro Glu Leu Phe Thr Thr Thr Pro Ala Leu Ala Ile Pro Lys Ala Ile
            100                 105                 110

Ser Asn Ala Gly Leu Glu Ser Ser His Val Asp Phe Phe Glu Ile Asn
            115                 120                 125

Glu Ala Phe Ser Ala Val Ala Leu Ala Asn Gln Lys Leu Leu Gly Ile
            130                 135                 140

Pro Ser Glu Lys Ile Asn Val His Gly Gly Ala Val Ser Leu Gly His
145                 150                 155                 160

Pro Leu Gly Cys Ser Gly Ala Arg Ile Leu Val Thr Leu Leu Gly Val
                165                 170                 175

Leu Arg Glu Lys Gly Gly Lys Ile Gly Val Ala Gly Val Cys Asn Gly
            180                 185                 190

Gly Gly Gly Ala Ser Val Leu Val Ser Asn Ser His Lys Lys His Trp
        195                 200                 205

Leu Glu Ala Leu Asp Met
    210
```

```
<210> SEQ ID NO 35
<211> LENGTH: 461
<212> TYPE: PRT
<213> ORGANISM: Arabidopsis thaliana

<400> SEQUENCE: 35

Met Ala Lys Asn Val Gly Ile Leu Ala Met Asp Ile Tyr Phe Pro Pro
  1               5                  10                  15

Thr Cys Val Gln Gln Glu Ala Leu Glu Ala His Asp Gly Ala Ser Lys
                 20                  25                  30

Gly Lys Tyr Thr Ile Gly Leu Gly Gln Asp Cys Leu Ala Phe Cys Thr
             35                  40                  45

Glu Leu Glu Asp Val Ile Ser Met Ser Phe Asn Ala Val Thr Ser Leu
         50                  55                  60

Phe Glu Lys Tyr Lys Ile Asp Pro Asn Gln Ile Gly Arg Leu Glu Val
 65                  70                  75                  80

Gly Ser Glu Thr Val Ile Asp Lys Ser Lys Ser Ile Lys Thr Phe Leu
                 85                  90                  95

Met Gln Leu Phe Glu Lys Cys Gly Asn Thr Asp Val Glu Gly Val Asp
            100                 105                 110

Ser Thr Asn Ala Cys Tyr Gly Gly Thr Ala Ala Leu Leu Asn Cys Val
            115                 120                 125

Asn Trp Val Glu Ser Asn Ser Trp Asp Gly Arg Tyr Gly Leu Val Ile
            130                 135                 140

Cys Thr Asp Ser Ala Val Tyr Ala Glu Gly Pro Ala Arg Pro Thr Gly
145                 150                 155                 160

Gly Ala Ala Ile Ala Met Leu Ile Gly Pro Asp Ala Pro Ile Val
                165                 170                 175

Phe Glu Ser Lys Leu Arg Ala Ser His Met Ala His Val Tyr Asp Phe
            180                 185                 190

Tyr Lys Pro Asn Leu Ala Ser Glu Tyr Pro Val Val Asp Gly Lys Leu
            195                 200                 205

Ser Gln Thr Cys Tyr Leu Met Ala Leu Asp Ser Cys Tyr Lys His Leu
210                 215                 220

Cys Asn Lys Phe Glu Lys Ile Glu Gly Lys Glu Phe Ser Ile Asn Asp
225                 230                 235                 240

Ala Asp Tyr Ile Val Phe His Ser Pro Tyr Asn Lys Leu Val Gln Lys
                245                 250                 255

Ser Phe Ala Arg Leu Leu Tyr Asn Asp Phe Leu Arg Asn Ala Ser Ser
            260                 265                 270

Ile Asp Glu Ala Ala Lys Glu Lys Phe Thr Pro Tyr Ser Ser Leu Thr
            275                 280                 285

Leu Asp Glu Ser Tyr Gln Ser Arg Asp Leu Glu Lys Val Ser Gln Gln
            290                 295                 300

Ile Ser Lys Pro Phe Tyr Asp Ala Lys Val Gln Pro Thr Thr Leu Ile
305                 310                 315                 320

Pro Lys Glu Val Gly Asn Met Tyr Thr Ala Ser Leu Tyr Ala Ala Phe
                325                 330                 335

Ala Ser Leu Ile His Asn Lys His Asn Asp Leu Ala Gly Lys Arg Val
            340                 345                 350

Val Met Phe Ser Tyr Gly Ser Gly Ser Thr Ala Thr Met Phe Ser Leu
            355                 360                 365

Arg Leu Asn Asp Asn Lys Pro Pro Phe Ser Ile Ser Asn Ile Ala Ser
            370                 375                 380
```

```
-continued

Val Met Asp Val Gly Gly Lys Leu Lys Ala Arg His Glu Tyr Ala Pro
385                 390                 395                 400

Glu Lys Phe Val Glu Thr Met Lys Leu Met Glu His Arg Tyr Gly Ala
            405                 410                 415

Lys Asp Phe Val Thr Thr Lys Glu Gly Ile Ile Asp Leu Leu Ala Pro
            420                 425                 430

Gly Thr Tyr Tyr Leu Lys Glu Val Asp Ser Leu Tyr Arg Arg Phe Tyr
        435                 440                 445

Gly Lys Lys Gly Glu Asp Gly Ser Val Ala Asn Gly His
450                 455                 460
```